(12) United States Patent
Sawkey et al.

(10) Patent No.: US 9,446,264 B2
(45) Date of Patent: Sep. 20, 2016

(54) SYSTEM AND METHOD FOR PATIENT-SPECIFIC MOTION MANAGEMENT

(71) Applicant: Varian Medical Systems, Inc., Palo Alto, CA (US)

(72) Inventors: Daren Sawkey, Palo Alto, CA (US); Michelle M. Svatos, Oakland, CA (US); Corey Zankowski, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 377 days.

(21) Appl. No.: 13/960,642

(22) Filed: Aug. 6, 2013

(65) Prior Publication Data

US 2015/0045604 A1 Feb. 12, 2015

(51) Int. Cl.
*A61N 5/00* (2006.01)
*A61N 5/10* (2006.01)

(52) U.S. Cl.
CPC ................... *A61N 5/1068* (2013.01)

(58) Field of Classification Search
CPC ........ A61N 5/00; A61N 5/10; A61N 5/1048; A61N 5/1064; A61N 5/1068
USPC .......................................................... 600/1–8
See application file for complete search history.

(56) References Cited

PUBLICATIONS

Mischa Hoogeman et al., "Clinical Accuracy of the Respiratory Tumor Tracking System of the Cyberknife: Assessment by Analysis of Log Files", Physics Contribution, I.J. Radiation Oncology, Biology, Physics, vol. 74, No. 1, 2009.
Geoffrey D Hugo et al., "Population and patient-specific target margins for 4D adaptive radiotherapy to account for intra-and inter-fraction variation in lung tumour position", Institute of Physics Publishing, Physics in Medicine and Biology, Phys. Med. Biol. 52, 2007, 19 pages.
Marcel van Herk, Ph.D., "The probability of Correct Target Dosage: Dose-Population Histograms for Deriving Treatment Margins in Radiotherapy", Physics Contributions, Int. J. Radiation Oncology Biology, Physics, vol. 47, No. 4, 2000, 15 pages.

*Primary Examiner* — John Lacyk
(74) *Attorney, Agent, or Firm* — Vista IP Law Group, LLP

(57) ABSTRACT

A medical method includes: determining a first probability density function related to a first uncertainty in hitting a target in a treatment of the target; determining a second probability density function related to a second uncertainty, wherein the first uncertainty is attributable to a first source of uncertainty, and the second uncertainty is attributable to a second source of uncertainty that is different from the first source of uncertainty; processing at least the first probability density function and the second probability density function using a processing unit; and outputting a result of the processing.

57 Claims, 14 Drawing Sheets

| Trace | Position [mm] | | | Velocity [mm/s] | |
|---|---|---|---|---|---|
| | Peak-peak amplitude | RMS amplitude | Motion-encompassing margins | Maximum magnitude | RMS |
| a | 15.3 | 4.4 | 6.6 | 30.2 | 7.2 |
| b | 36.8 | 8.2 | 14.9 | 41.5 | 12.2 |
| c | 23.1 | 6.7 | 10.2 | 36.6 | 7.8 |
| d | 24.1 | 5.8 | 10.8 | 31.6 | 6.3 |
| e | 18.2 | 3.9 | 7.6 | 34.2 | 11.4 |
| f | 14.6 | 4.0 | 6.6 | 29.6 | 7.4 |
| g | 17.2 | 3.9 | 7.2 | 29.8 | 4.8 |
| h | 15.0 | 3.6 | 6.1 | 34.1 | 9.8 |
| i | 20.5 | 5.1 | 9.4 | 64.1 | 13.6 |
| j | 23.6 | 8.0 | 11.2 | 58.5 | 16.7 |
| Mean | 20.8 | 5.4 | 9.1 | 39.0 | 9.7 |
| Pop.std.dev. | 6.3 | 1.6 | 2.6 | 11.7 | 3.5 |

FIG. 6

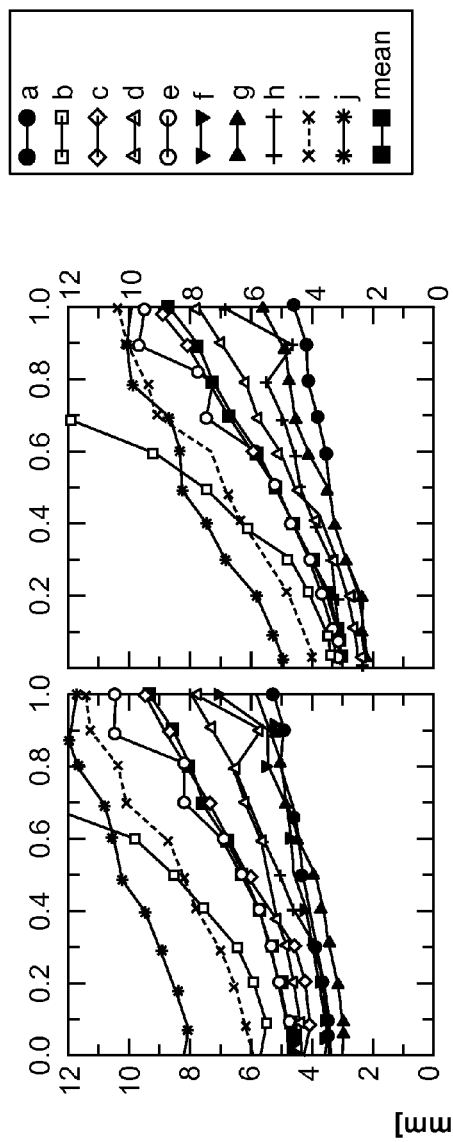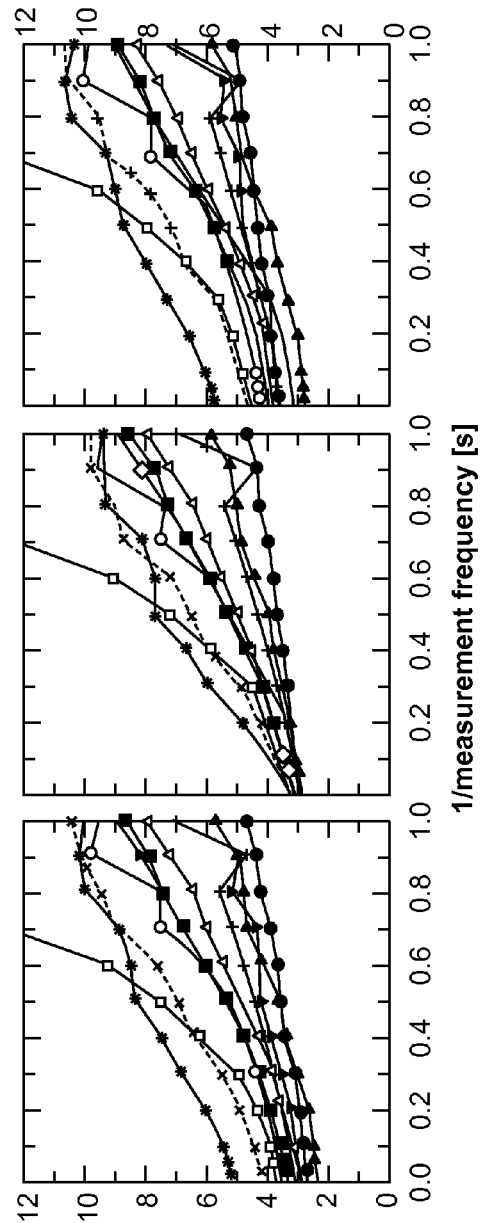
FIG. 12A FIG. 12B FIG. 12C FIG. 12D FIG. 12E

SYSTEM AND METHOD FOR PATIENT-SPECIFIC MOTION MANAGEMENT

FIELD

An embodiment described herein relates to treatment planning, and more specifically, to method and system for treatment planning.

BACKGROUND

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. In certain types of radiotherapy, the irradiation volume can be restricted to the size and shape of the tumor or targeted tissue region to avoid inflicting unnecessary radiation damage to healthy tissue. For example, conformal therapy is a radiotherapy technique that is often employed to optimize dose distribution by conforming the treatment volume more closely to the targeted tumor.

Normal physiological movement represents a limitation in the clinical planning and delivery of conventional radiotherapy and conformal therapy. Normal physiological movement, such as respiration or heart movement, can cause a positional movement of the tumor or tissue region undergoing irradiation. If the radiation beam has been shaped to conform the treatment volume to the exact dimensions of a tumor, then movement of that tumor during treatment could result in the radiation beam not being sufficiently sized or shaped to fully cover the targeted tumoral tissue.

One method to account for the target motion is to simply open up the field aperture to ensure that the radiation volume covers the entire extent of the tumor motion. The problem with this approach is that it irradiates an unnecessarily large volume of healthy tissue.

In another method, physiological gating of the radiation beam during treatment may be performed, with the gating signal synchronized to the movement of the tumor or of a surrogate of the tumor. Such technique may reduce the volume of healthy tissue being exposed to high dose radiation. In this approach, instruments are utilized to measure the physiological state of the patient with reference to the particular physiological movement being examined. For example, respiration has been shown to cause movements in the position of a lung tumor in a patient's body. If radiotherapy is being applied to the lung tumor, then a position sensor can be attached to the patient to measure the patient's respiration cycle. The radiation beam can be gated based upon certain threshold points within the measured respiratory cycle, such that the radiation beam is disengaged during periods in the respiration cycle that correspond to excessive movement of the lung tumor. In some cases, when gating technique is used, the beam may be gated off for a significant amount of time, thereby extending the length of the treatment session.

During treatment, target motion may result in dose intended for a lesion being delivered to normal tissue and organs at risk instead. This requires a strategic treatment decision to mitigate the effect of any anticipated motion in order to preserve the treatment intent. Many methods have been proposed or developed to reduce the dose to normal tissue, including pausing the treatment beam while the lesion is outside the beam (gating), and moving the beam to follow the lesion motion (tracking). It may be difficult, however, to compare the effectiveness of different strategies, and to determine the best strategy for a given patient. In part, this stems from the stochastic nature of the events causing the motion. Furthermore, factors contributing to the relative effectiveness, or ineffectiveness, of each treatment strategy are not always apparent prior to treatment.

SUMMARY

In some embodiments, methods and systems are provided for combining multiple uncertainties in a medical process (e.g., radiotherapy process). The uncertainties are combined through convolution to make a prediction of how accurate a treatment will be (e.g., probability of hitting a target). With such prediction, various treatment delivery scenarios may be compared, such as whether to perform gating or tracking, and the best treatment delivery plan may be determined for a patient. For example, with such technique, it may be determined that the additional hassle (extended treatment time) of treating with gating is not worth it if it does not greatly improve a predicted treatment result (e.g., if a predicted treatment result does not improve by more than a prescribed threshold).

In accordance with some embodiments, a medical method includes: determining a first probability density function related to a first uncertainty in hitting a target in a treatment of the target; determining a second probability density function related to a second uncertainty, wherein the first uncertainty is attributable to a first source of uncertainty, and the second uncertainty is attributable to a second source of uncertainty that is different from the first source of uncertainty; processing at least the first probability density function and the second probability density function using a processing unit; and outputting a result of the processing. For example, in some embodiments, the first uncertainty may be the likelihood of finding a target at a given location as a function of the target motion. Also, for example, in some embodiments, the second uncertainty may be that due to variations in daily patient positioning for treatment. In other embodiments, the first and second probability density functions may describe other uncertainties.

Optionally, the act of processing comprises combining the first and second probability density functions by convolution to determine a composite probability density function.

Optionally, the method further includes determining a margin based on the composite probability density function.

Optionally, the method further includes determining a volume that encompasses a level of certainty derived from the composite probability density function.

Optionally, the act of determining the volume comprises determining a margin expansion.

Optionally, the result comprises the composite probability density function.

Optionally, the act of processing comprises performing a calculation using a margin as an optimization variable.

Optionally, the first probability density function is based on a motion trace.

Optionally, the motion trace is created using one or more external markers.

Optionally, the motion trace is created using one or more internal markers.

Optionally, the motion trace represents a breathing motion, a cardiac motion, or an irregular motion.

Optionally, the motion trace represents a motion of a patient for which the first probability density function is determined.

Optionally, the first probability density function is determined for a first patient, and the motion trace represents a motion of a second patient or a modeled motion.

Optionally, the first uncertainty is attributable to an accuracy of a device that measures positions.

Optionally, the first uncertainty is attributable to an accuracy of a correlation between a marker position and a tissue position.

Optionally, the first uncertainty is attributable to an accuracy in a prediction of a future position.

Optionally, the first uncertainty is attributable to an energy delivery accuracy of a treatment machine. By means of non-limiting examples, energy delivery accuracy may refer to spatial accuracy, timing accuracy, etc., or combination of the foregoing.

Optionally, the first uncertainty relates to a gating window.

Optionally, the result is output during a treatment planning session.

Optionally, the result is output during a treatment session.

Optionally, the result comprises a ranking of different motion management strategies.

Optionally, the different motion management strategies are ranked based on different respective margins, or based on different volumes derived from the different respective margins.

Optionally, the result comprises a margin.

Optionally, the result comprises information regarding a beam aperture margin.

Optionally, the method further includes: obtaining motion data during a treatment session; and adjusting a beam aperture based on the information regarding the beam aperture margin.

Optionally, the result comprises a volume to be treated.

Optionally, the result comprises a volume of healthy tissue.

Optionally, the method further comprises adjusting a dose rate based on the result during a treatment session.

An apparatus for use in a medical field includes a processing unit configured for: determining a first probability density function related to a first uncertainty in hitting a target in a treatment of the target; determining a second probability density function related to a second uncertainty, wherein the first uncertainty is attributable to a first source of uncertainty, and the second uncertainty is attributable to a second source of uncertainty that is different from the first source of uncertainty; processing at least the first probability density function and the second probability density function; and outputting a result of the processing.

Optionally, the processing unit is configured to perform the act of processing by combining the first and second probability density functions by convolution to determine a composite probability density function.

Optionally, the processing unit is further configured for determining a margin based on the composite probability density function.

Optionally, the processing unit is further configured for determining a volume that encompasses a level of certainty derived from the composite probability density function.

Optionally, the processing unit is configured for determining a margin expansion for determining the volume.

Optionally, the result comprises the composite probability density function.

Optionally, the processing unit is configured to perform the act of processing comprises performing a calculation using a margin as an optimization variable.

Optionally, the processing unit is configured to receive a motion trace, and the processing unit is configured to determine the first probability density function based on a motion trace.

Optionally, the motion trace is created using one or more external markers.

Optionally, the motion trace is created using one or more internal markers.

Optionally, the motion trace represents a breathing motion, a cardiac motion, or an irregular motion.

Optionally, the motion trace represents a motion of a patient for which the first probability density function is determined.

Optionally, the first probability density function is for a first patient, and the motion trace represents a motion of a second patient or a modeled motion.

Optionally, the first uncertainty is attributable to an accuracy of a device that measures positions.

Optionally, the first uncertainty is attributable to an accuracy of a correlation between a marker position and a tissue position.

Optionally, the first uncertainty is attributable to an accuracy in a prediction of a future position.

Optionally, the first uncertainty is attributable to an energy delivery accuracy of a treatment machine. By means of non-limiting examples, energy delivery accuracy may refer to spatial accuracy, timing accuracy, etc., or combination of the foregoing.

Optionally, the first uncertainty relates to a gating window.

Optionally, the processing unit is configured to output the result during a treatment planning session.

Optionally, the processing unit is configured to output the result during a treatment session.

Optionally, the result comprises a ranking of different motion management strategies.

Optionally, the processing unit is configured to rank the different motion management strategies based on different respective margins.

Optionally, the result comprises a margin.

Optionally, the result comprises information regarding a beam aperture margin.

Optionally, the processing unit is further configured for: obtaining motion data during a treatment session; and adjusting a beam aperture based on the information regarding the beam aperture margin.

Optionally, the result comprises a volume to be treated.

Optionally, the result comprises a volume of healthy tissue.

Optionally, the processing unit is further configured to adjust a dose rate based on the result during a treatment session.

A computer product includes a non-transitory medium storing a set of instructions, an execution of which causes an image processing method to be performed, the method comprising: determining a first probability density function related to a first uncertainty in hitting a target in a treatment of the target; determining a second probability density function related to a second uncertainty, wherein the first uncertainty is attributable to a first source of uncertainty, and the second uncertainty is attributable to a second source of uncertainty that is different from the first source of uncertainty; processing at least the first probability density function and the second probability density function; and outputting a result of the processing.

Other and further aspects and features will be evident from reading the following detailed description.

BRIEF DESCRIPTION OF THE DRAWINGS

The drawings illustrate the design and utility of various features described herein, in which similar elements are referred to by common reference numerals. These drawings are not necessarily drawn to scale. In order to better appreciate how the above-recited and other advantages and objects are obtained, a more particular description will be rendered, which are illustrated in the accompanying drawings. These drawings depict only exemplary features and are not therefore to be considered limiting in the scope of the claims.

FIG. 6 illustrates examples of characteristics of motion traces.

FIG. 12A-12E illustrates examples of margins for five different treatment strategies.

DETAILED DESCRIPTION

Figure 1:
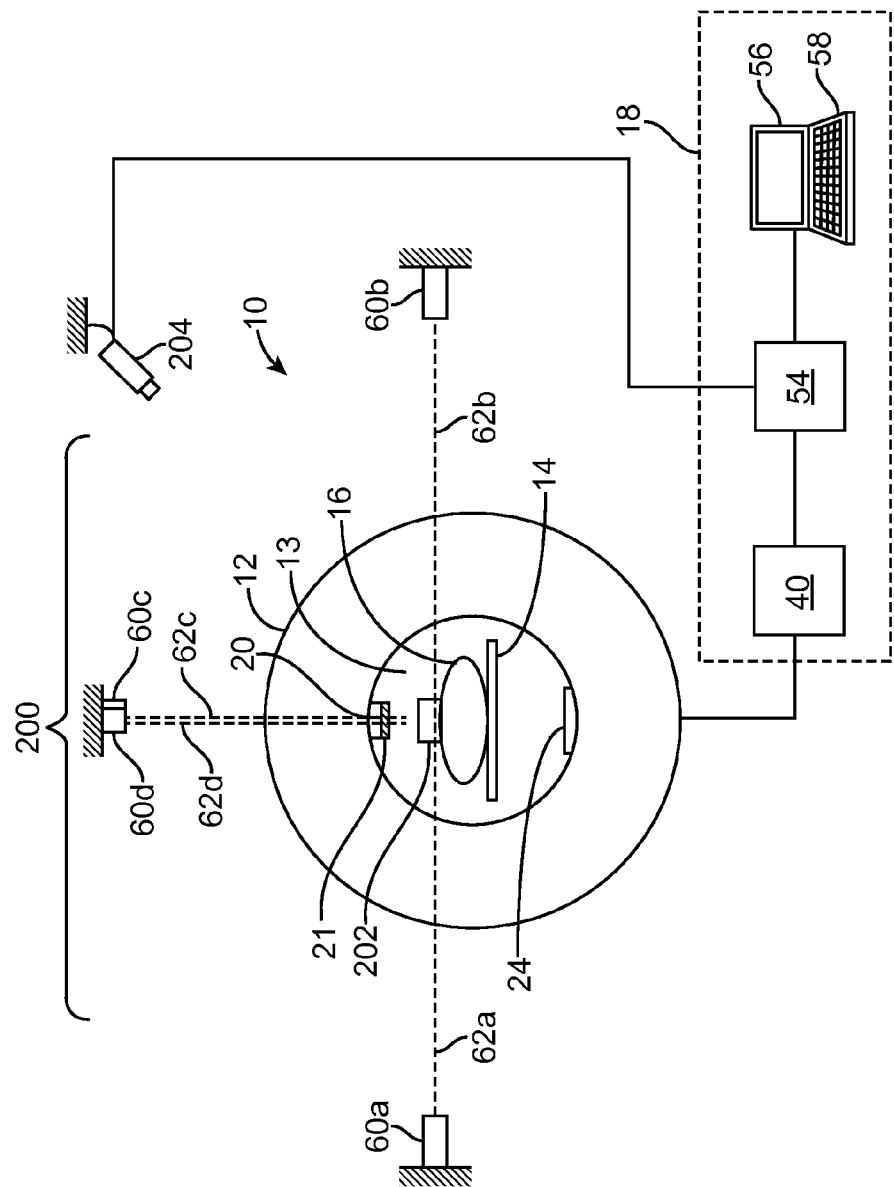
FIG. 1 illustrates a radiation system being used with a marker system.

Various features are described hereinafter with reference to the figures. It should be noted that the figures are not drawn to scale and that the elements of similar structures or functions are represented by like reference numerals throughout the figures. It should be noted that the figures are only intended to facilitate the description of the features. They are not intended as an exhaustive description of the claimed invention or as a limitation on the scope of the claimed invention. In addition, an illustrated feature needs not have all the aspects or advantages shown. An aspect or an advantage described in conjunction with a particular feature is not necessarily limited to that feature and can be practiced in any other features even if not so illustrated, or if not so explicitly described.

Radiation System

FIG. 1 illustrates a radiation system 10. The system 10 includes a gantry 12 having an opening (or bore) 13, a patient support 14 for supporting a patient 16, and a control system 18 for controlling an operation of the gantry 12. In the illustrated embodiments, the gantry 12 has a slip-ring configuration (donut shape). Alternatively, the gantry 12 can have other configurations, such as an arm (e.g., a C-arm) configuration. The system 10 also includes a radiation source (e.g., x-ray source) 20 that projects a beam of radiation towards the patient 16, and a collimator 21 for changing a shape of the beam. The system 10 also includes a detector 24 on an opposite side of the gantry 12, which in some cases, may be used to receive radiation exiting from the patient 16, and generate image(s) using the received radiation. The detector 24 has a plurality of sensor elements configured for sensing a x-ray that passes through the patient 16. Each sensor element generates an electrical signal representative of an intensity of the x-ray beam as it passes through the patient 16. In other embodiments, the system 10 does not include the detector 24.

In the illustrated embodiments, the radiation source 20 is a treatment radiation source for providing treatment energy. In other embodiments, the radiation source 20 may be a diagnostic radiation source for providing diagnostic energy (e.g., energy that is suitable for generating an image). In further embodiments, the radiation source 20 can be configured to selectively provide treatment energy and diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV.

The control system 18 includes a processor 54, such as a computer processor, coupled to a source rotation control 40. The control system 18 may also include a monitor 56 for displaying data and an input device 58, such as a keyboard or a mouse, for inputting data. During a scan to acquire x-ray projection data (e.g., cone beam CT image data), the source 20 rotates about the patient 16. The rotation of the source 20 and the operation of the radiation source 20 are controlled by the source rotation control 40, which provides power and timing signals to the radiation source 20 and controls a rotational speed and position of the source 20 based on signals received from the processor 54. Although the control 40 is shown as a separate component from the gantry 12 and the processor 54, in alternative embodiments, the control 40 can be a part of the gantry 12 or the processor 54.

In some embodiments, the system 10 may be a treatment system configured to deliver treatment radiation beam towards the patient 16 at different gantry angles. During a treatment procedure, the source 20 rotates around the patient 16 and delivers treatment radiation beam from different gantry angles towards the patient 16. While the source 20 is at different gantry angles, the collimator 21 is operated to change the shape of the beam to correspond with a shape of the target tissue structure. For example, the collimator 21 may be operated so that the shape of the beam is similar to a cross sectional shape of the target tissue structure. In another example, the collimator 21 may be operated so that different portions of the target tissue structure receive different amount of radiation (as in an IMRT procedure).

As shown in the figure, the radiation system 10 is used with a marker system 200 that includes a marker block 202 and a camera 204. The camera 204 is coupled to the processor 54, which in accordance with some embodiments, may be a part of the marker system 200. Alternatively, instead of the processor 54, the camera 204 may be coupled to another processor (not shown). Also, in other embodiments, the marker system 200 may not include the camera 204. During use, the marker block 202 is coupled to the patient 16 (e.g., placed on the patient's chest, abdomen, or another body part), and the camera 204 is used to view the marker block 202. The camera 204 transmits image data to the processor 54, which processes the image data to determine a position and/or orientation of the marker block 202.

As shown in the figure, four lasers 60a-60d are positioned adjacent to the system 10. The lasers 60a-60d are configured to generate respective laser beams 62a-62d, which may be used to align the marker block 202 (and therefore, the patient 16) at a desired location. In the illustrated embodiments, lasers 60a, 60b are configured to generate and project laser beams 62a, 62b from opposite sides of the marker block 202, laser 60c is configured to generate and project laser beam 62c from above the marker block 202, and laser 60d is configured to generate and project laser beam 62d downwardly at an angle onto the marker block 202. In other embodiments, the lasers 60 may be configured to project the laser beams 62 from other directions. Each laser 60 may be mounted to any structure, such as a wall, a ceiling, a patient support, or another device. Although four lasers 60 are shown, in other embodiments, more or less than four lasers 60 may be used. For example, in other embodiments, only lasers 60a-60c are used.

In operation, the marker block 202 is coupled to the patient 16. The marker block 202 may be placed on the patient 16, and/or may be secured to the patient 16 via a securing mechanism (e.g., adhesive, strap, clip, etc.). The camera 204, which is directed at patient 16, captures and detects the markers 208. The camera 204 generates video images that show the position of the markers (not shown) on the marker block 202 within its video frame. The generated video images are sent to a processing unit (e.g., processor 54, or another processor) for further processing. The processing unit receives video images from the camera 204. The processing unit first processes each video image from the camera 204 to identify images of the markers 208 in the image frame. Based on the determined position of the markers 208, and the known relative positions among the markers 208, the processing unit then determines the position (X, Y, Z) and/or orientation ($\theta_X$, $\theta_Y$, $\theta_Z$) of the marker block 202. In some embodiments, information regarding the location and orientation of the camera 204 is provided to the processing unit to facilitate the computations of the position and/or orientation of the marker block 202.

In some embodiments, the determined position and/or orientation of the marker block 202 can then be used to position the patient 16 at desired position and/or orientation. For example, the determined position of the marker block 202 may be compared with a prescribed position of the marker block 202. In such cases, if the determined position of the marker block 202 matches with the prescribed position, the patient 16 is then considered to be correctly positioned. On the other hand, if the determined position of the marker block 202 does not match the prescribed position, the patient 16 is then positioned (e.g., by moving the patient support 14) until the marker block 202 position matches with the prescribed position.

In other embodiments, the determined position and/or orientation of the marker block 202 can be used to determine the position of at least a portion of the patient 16. In such cases, the relative spatial relationship between the marker block 202 and the patient 16 is known or predetermined. As such, once the marker block 202 position is determined, the position of the portion of the patient 16 can then be determined (e.g., via the processing unit) based on the relative spatial relationship between the marker block 202 and the patient 16. In some embodiments, by continuously determining the position of the portion of the patient 16 in real time, the portion of the patient 16 can be tracked in real time. The tracked position of the patient 16 may be used to gate an application of radiation provided by the system 10. In further embodiments, the tracked position of the patient 16 may be used to perform tracking of a target region while an intensity modulated radiation therapy (IMRT) is being performed. In IMRT, a multi-leaf collimator is operated such that a first portion of the target region receives more radiation than a second portion of the target region during a treatment session.

In further embodiments, the determined position of the marker block 202 can be used to determine a level of activity accomplished by the patient 16. For example, if the marker block 202 is placed on the patient's chest, then the determined position of the marker block 202 can be used to determine a level of breathing performed by the patient 16. In some cases, by determining a plurality of positions of the marker block 202 over a period of time, the processing unit can be configured to obtain a plurality of amplitude points that correspond to the patient's levels of breathing at various time points in that period. The determined amplitude points may be used to gate an execution of a procedure, such as, to gate an application of a treatment radiation to the patient 16 for treatment, or to gate an application of an imaging radiation to the patient 16 for imaging purpose. In other embodiments, the determined positions of the marker block 202 (or the amplitude points) may be used to gate a binning of image data, either in real time, or after the image data has been obtained. In further embodiments, the amplitude points may be used to perform tracking of a target region while IMRT is being performed.

In further embodiments, by determining a plurality of positions of the marker block 202 over a period of time, the processing unit can be configured to obtain a plurality of phase points that correspond to different levels of completeness of a breathing cycle at various time points. For example, a phase value may have a value from 0° to 360°, with 0° representing a beginning of a respiratory cycle, and 360° representing an end of the respiratory cycle. In some embodiments, the phase values between the beginning and the end of the respiratory cycle may vary linearly between 0° and 360°. Thus, for each breathing amplitude, the processing unit can determine the corresponding phase of the respiratory cycle.

In some embodiments, the determined phase values may be used to gate an execution of a procedure, such as, to gate an application of a treatment radiation to the patient 16 for treatment, or to gate an application of an imaging radiation to the patient 16 for imaging purpose. In further embodiments, the phase values may be used to perform tracking of a target region while IMRT is being performed.

Before a radiation treatment is performed on a patient, a treatment plan may be determined for the patient. When preparing the treatment plan, a certain margin may be prescribed around a target tissue structure. The margin may be a certain value determined to account for the uncertainty that the target tissue structure may be missed by the radiation beam. The uncertainty may be attributable to a variety of sources, such as an accuracy of the position determining device (e.g., the accuracy of the marker system 200, or another type of position/physiological state determining device, such as internal implantable markers), an accuracy of a correlation between a marker position and a tissue position, an accuracy in a prediction of a future position (e.g., in some cases, the marker system 200 may be used with an algorithm to predict a future position), an energy delivery accuracy of a treatment machine (which is related to one or more latencies, such as a latency in the operation of the machine, latency in signal processing, etc.), an accuracy in positioning the patient 16, a gating window, etc.

In some cases, the user may prescribe the margin in the treatment plan based on certain recommendation in the medical community. However, the user does not have any tools that allow the user to consider the individual sources of uncertainty in determining the margin for a treatment plan. As a result, the user also does not and cannot determine the margin quantitatively based on consideration of the different sources of uncertainty. The user also does not and cannot determine a margin that is specific for a patient, for a certain treatment machine, and for a certain treatment arrangement.

Figure 2:
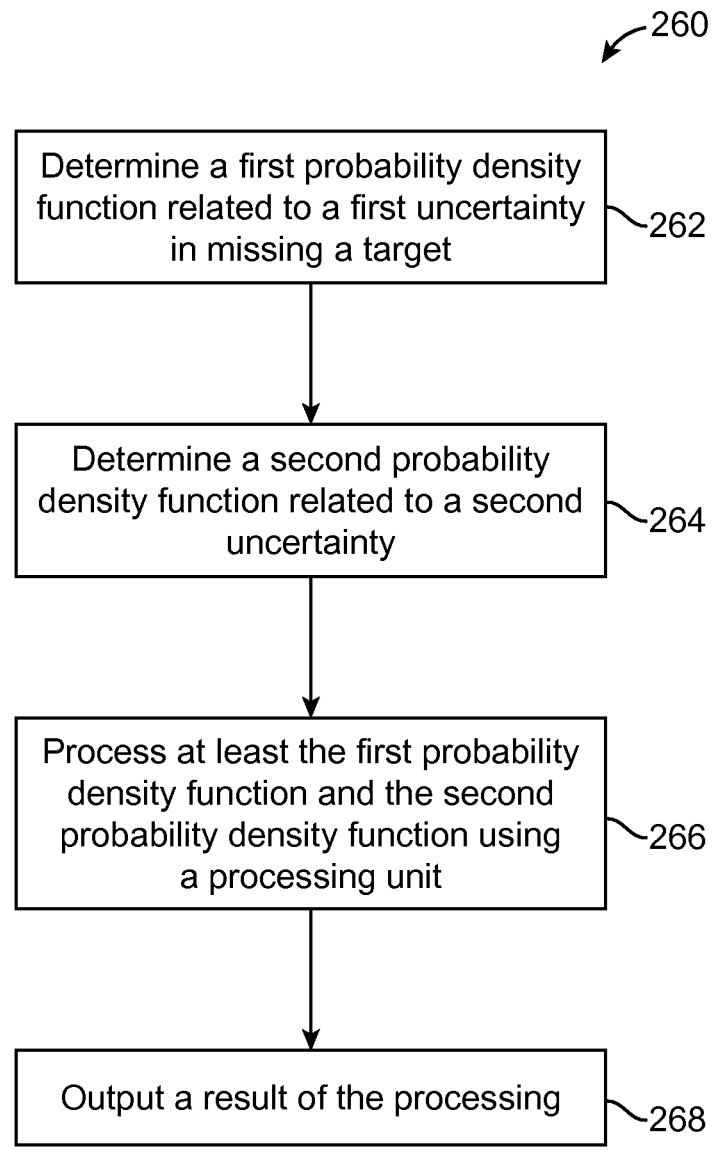
FIG. 2 illustrates a medical method in accordance with some embodiments.
Figure 4:
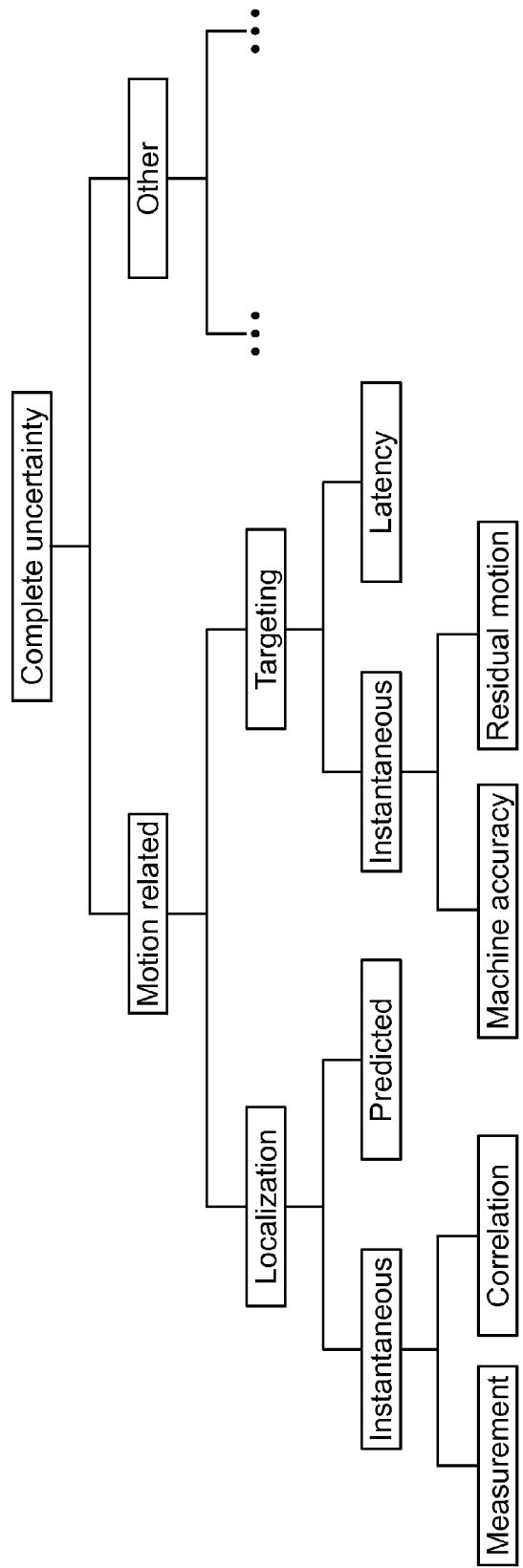
FIG. 4 illustrates an example of a classification of sources of uncertainty.

FIG. 2 illustrates a medical method 200 in accordance with some embodiments. As shown in the figure, the method 200 includes: determining a first probability density function related to a first uncertainty in hitting a target in a treatment of the target (item 262); determining a second probability density function related to a second uncertainty (item 264); processing at least the first probability density function and the second probability density function using a processing unit (item 266); and outputting a result of the processing (item 268). In some embodiments, the first uncertainty is attributable to a first source of uncertainty, and the second uncertainty is attributable to a second source of uncertainty that is different from the first source of uncertainty. By means of non-limiting examples, the first or second uncertainty may be attributable to an accuracy of a device that measures positions, an accuracy of a correlation between a marker position and a tissue position, an accuracy in a prediction of a future position, an energy delivery accuracy of a treatment machine, an accuracy in positioning a patient, or a gating window. There are lots of individual sources of uncertainty, and the concept of using a margin to account for motion has been established (ICRU 62, www.icru.org). Also, in some embodiments, the first uncertainty may be one of the uncertainties illustrated in FIG. 4, and the second uncertainty may be another one of the uncertainties illustrated in FIG. 4 that is different from the first uncertainty. FIG. 4 illustrates different uncertainties that are arranged in a certain hierarchy, which will be explained in further detail below.

It should be noted that an uncertainty in hitting a target may be a counter part of an uncertainty in missing a target. For example, a 95% probability of hitting target may be considered the same as a 5% probability of missing a target, and vice versa. Thus, a probability density function related to an uncertainty in hitting a target in a treatment of the target may also be considered a probability density function that is related to an uncertainty in missing the target.

Although the method 260 has been described as involving two probability density functions, in other embodiments, the method 260 may include determining more than two probability density functions that relate to different respective uncertainties.

In the illustrated embodiments, one or more of the items 262-268 in the method 260 may be performed by a processing unit. The processing unit may be a part of a treatment planning system, a part of a treatment system, or both. In other embodiments, the processing unit may be a standalone system that is separate from a treatment planning system and from a treatment system. In such cases, the processing unit may be configured to communicate with the treatment planning system and/or with the treatment system. The processing unit may be implemented using hardware, software, or both. By means of non-limiting examples, the processing unit may be one or more processors (e.g., ASIC processor(s), FPGA processor(s), general purpose processor (s), etc.). In one implementation, the processing unit may include a network of computers and/or databases. For example, the databases may store different respective probability density functions that are organized based on certain parameter(s).

In some embodiments, the act 262 of determining the first probability function may be achieved by the processing unit receiving the first probability function from a source (e.g., a medium, such as a database). In other embodiments, the act 262 of determining the first probability function may be achieved by the processing unit computing the probability function quantitatively. For example, in some embodiments, the processing unit may be configured to calculate a probability density function that indicates a spread of different margin values for a source of uncertainty.

Similarly, in some embodiments, the act 264 of determining the second probability function may be achieved by the processing unit receiving the second probability function from a source (e.g., a medium, such as a database). In other embodiments, the act 264 of determining the second probability function may be achieved by the processing unit computing the probability function quantitatively. For example, in some embodiments, the processing unit may be configured to calculate a probability density function that indicates a spread of different margin values for a source of uncertainty.

Also, in some embodiments, the act 266 of processing the first and second probability density functions comprises combining the first and second probability density functions by convolution (e.g., multiplication, addition, and/or integration, etc.) to determine a composite probability density function. In some embodiments, the method 200 may further include determining one or more margins by determining a minimum width that encompasses a desired area of the composite probability density function. In other embodiments, the act 266 of processing the first and second probability density functions may be accomplished by the processing unit associating the data of the first probability density function with data of the second probability density function. In further embodiments, the act 266 of processing may include performing a calculation using a margin as an optimization variable. Also, in some embodiments, the act 266 of processing the first and second probability density functions may result in a margin or a threshold for gating purposes.

In some embodiments, the act 268 of outputting the result may be achieved by the processing unit sending the result to a non-transitory medium for storing the result. In other embodiments, the act 268 of outputting the result may be achieved by the processing unit sending the result to a screen for displaying the result to a user.

In some embodiments, the result in item 268 may be the composite probability density function that is obtained by combining two or more individual probability density functions for the respective sources of uncertainty. In other embodiments, the result may include one or more margins that are derived from the composite probability density function. For example, a margin may be calculated based on certain area underneath the composite probability density function. In still other embodiments, the result may include a ranking of different motion management strategies that are determined based on different probability density functions.

Optionally, the different motion management strategies may be ranked based on different respective margins, or based on different volumes derived from the different respective margins. Also, in some embodiments, the result may include PDFs constructed from residuals, margins for different motion traces, PDFs of motion traces, margins due to duty cycle for a treatment (e.g., a gated treatment), margins due to latency, margins for different treatment strategies, means of margins for different treatment strategies, or any combination of the foregoing. In further embodiments, the result in item 268 may be multiple probability density functions that are displayed together in a same screen. In still further embodiments, the result in item 268 may be any of the type of information, or any combination of the type of information, presented in FIGS. 7-13, which will be discussed in further detail below.

In some embodiments, the first probability density and/or the second probability density function may be determined for one or more motion traces. For example, in some embodiments, one or more motion traces for a patient may be input to the processing unit, and the processing unit may determine the first probability density function based on the motion trace(s). In other embodiments, the motion traces may be for different patients.

The motion trace may represent any motion of a patient, such as a breathing motion, a cardiac motion, or an irregular motion. In some embodiments, the motion trace is created using one or more external markers. For example, the one or more external markers may be one or more markers (individually or on a block) coupled to the patient, or one or more landmarks on the patient. The marker(s) may be passive marker(s), or may be active marker(s) (e.g., marker(s) that emits a signal, such as light signal). In other embodiments, the motion trace is created using one or more internal markers. For example, the one or more internal markers may be one or more passive markers (such as radio opaque marker(s)), or one or more active markers (such as marker(s) that emits a signal, e.g., a RF signal, a magnetic signal, an ultrasound signal, etc.).

In some embodiments, the motion trace obtained may be the motion trace of the patient for which treatment is being considered. In such cases, the first probability function is for the same patient for which the motion trace is created. In other embodiments, the motion trace may represent a motion of another patient, or may represent a modeled motion.

In some embodiments, the method 200 may be performed during a treatment planning session, and the result of the analysis performed by the processing unit may be output during the treatment planning session.

In other embodiments, the method 200 may be performed during a treatment session (or simulation), and the result of the analysis performed by the processing unit may be output during the treatment session. In some cases, the method may further include adjusting a dose rate based on the result (provided by the processing unit) during a treatment session. Also, in some embodiments, the result provided by the processing unit may include information regarding a beam aperture margin. In such cases, the method 200 may further include adjusting a beam aperture during the treatment session based on the information regarding the beam aperture margin.

Also, in some embodiments, the result (determined based on the composite probability density function) provided by the processing unit may include information regarding a volume involved during treatment. The volume may be a target, a volume of healthy tissue, or a combination of both. In some embodiments, the volume may be obtained by determining a margin expansion, and increasing a volume of interest by the margin expansion. In some embodiments, the determined volume may encompass a level of certainty derived from the composite probability density function. In one or more embodiments, the processing unit may optionally be configured to minimize the volume of healthy tissue located in a high-dose region of the treatment site. Also, in some embodiments, a margin (e.g., a margin expansion) may be determined based on the composite probability density function. The margin provides an envelope in three dimension around the tumor such that the probability of finding the tumor within the volume at any given time is some defined level of certainty (e.g., 95% chance of finding a tumor at any pixel within the volume defined by the CTV plus margin.) Any number of independent probability density functions may be combined to form the composite probability density function. By means of non-limiting examples, one or more of the following probability density functions (PDFs) may be convolved together using the processing unit to create a composite probability density function: a PDF for motion uncertainty, a PDF for setup uncertainty, a PDF for measurement uncertainty, a PDF for contouring uncertainty, etc. From the composite PDF, the processing unit may derive the high-dose volume such that the treated volume achieves a defined level of certainty of containing the tumor volume.

EXAMPLE

I. Introduction of Example

As discussed, target motion can result in dose intended for a lesion being delivered to normal tissue and organs at risk instead. In some embodiments, a strategic treatment decision may be used to mitigate the effect of any anticipated motion in order to preserve the treatment intent. In some cases, pausing the treatment beam while the lesion is outside the beam (an example of gating), and/or moving the beam to follow the lesion motion (an example tracking) may be techniques for mitigating the above effect. It can be difficult, however, to compare the effectiveness of different strategies, and to determine the best strategy for a given patient. In part, this stems from the stochastic nature of the events causing the motion. Furthermore, factors contributing to the relative effectiveness, or ineffectiveness, of each treatment strategy may not always be apparent prior to treatment. In the following example, an example of a systematic and quantitative method of comparing motion management strategies is described. This method produces a recommendation of a strategy for a particular patient, or a population, and allows isolation of the factors contributing to unplanned extraneous dose. The example discussed below may be considered an example of the method 260 of FIG. 2.

In the following example, margins are determined for several motion management strategies for a variety of motion traces that were previously published. In each case, a motion margin that accounts for the motion of the center of mass of the clinical treatment volume (CTV) is calculated. Actual treatment margins would include other sources of uncertainty, and be larger. For each motion management strategy, treatments of lesions moving according to the motion traces are simulated. For each simulated treatment, the motion margin is the minimum value such that the radiation hits the target (1) some percentage (e.g., 95%) of fractions, or (2) during some percentage (e.g., 95%) of the treatment time (e.g., total energy delivery duration). In other embodiments, the value may be different from 95%. Also, in other embodiments, the percentage may be a percentage of dose delivered to target.

In order to determine the motion margin, the sources of uncertainty potentially leading to a geometric miss are first considered in isolation. Other sources of uncertainty are assumed to be negligible. Probability density functions (PDF) are generated for each source of uncertainty, giving the probabilities of displacements between the beam and CTV. For some sources of uncertainty, PDFs may be based on values taken from the literature. For others, PDFs may be calculated by simulating treatment of a CTV moving according to the motion trace.

Motion management strategies are then studied by combining the individual PDFs by convolution. Motion margins may be determined from the combined PDF for each motion management strategy for each motion trace, and the motion margins for the individual traces may then be averaged. Motion management strategies may be compared based on the mean motion margins. Possible reductions to the individual sources of uncertainty may be considered. These reductions may be incorporated into the combined PDF for each motion management strategy, and new motion margins may be calculated.

2. Technique

Figure 3:
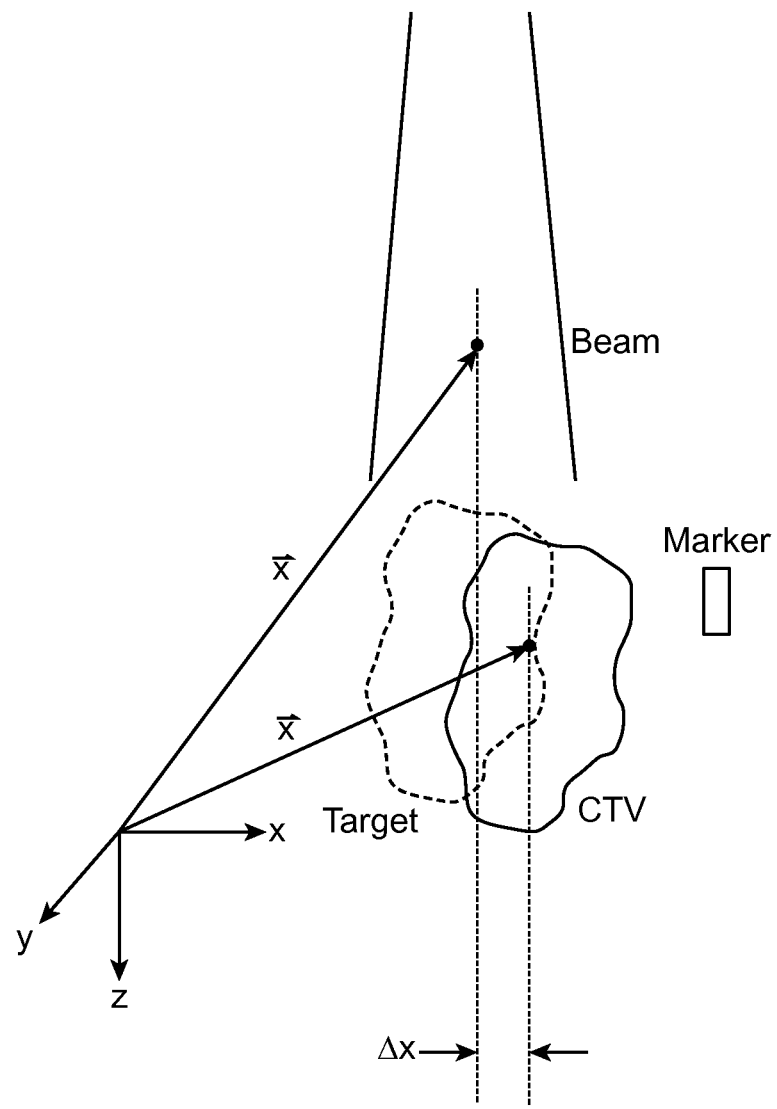
FIG. 3 illustrates a relationship between a target and a CTV.

Consider a treatment with a C-arm gantry linac with a multi-leaf collimator (MLC) that may or may not move. The method described here may readily generalize to other geometries. Consider a beamlet of a step-and-shoot field— that is, the size and shape of the MLC-defined field does not change during delivery of the beamlet. Extension to sliding window or VMAT treatments may be done by considering multiple beamlets. Consider a rigid CTV that does not rotate, but may exhibit translational motion. Suppose that a reference point in the CTV may be precisely defined. In the illustrated example, a coordinate system is defined such that the beam axis is directed along the positive z axis. Denote the position of the CTV reference point as $x=(x,y,z)$, where boldface denotes a vector (see FIG. 3).

In the exemplary method, treatment may proceed with simultaneous measurement of the position of a marker. The position of the CTV may be inferred from the position of the marker. The inferred position is the target to which a radiation beam defined by the MLC is directed. A reference point in the beam may be defined at coordinates $x'=(x',y',z0')$, where the component in the z direction (along the beam axis) is arbitrary. The CTV and beam may both move, so x and x' are functions of time t. Motions in each direction may be assumed to be independent. In the x direction, the difference between beam and CTV positions is $\Delta x(t)=x'(t)-x(t)$.

$\Delta x(t)$ may take a range of values over the beam-on time of the beamlet. The probability that $\Delta x(t)$ is between x and x+dx at a particular time is given by $P(x)\,dx$, where $P(x)$ is the probability density function of the motion in the x direction. The reference point x' may be chosen such that the center of mass of the PDF is zero. In some cases, PDFs may be normalized such that their integral was 1.

3. Sources of Uncertainty

In the illustrated example, several sources of uncertainty are considered. Sources of uncertainty that contribute to the required margins are categorized in FIG. 4. The highest level division is between the sources of uncertainty that relate to delivering radiation to a moving CTV, and those from other sources. The sources related to motion are divided into locating the CTV, and hitting the target. Sources of uncertainty in locating the CTV are divided into the instantaneous measurement of position, and the prediction of the position at future times. Uncertainties in the instantaneous measurement of position included measuring the position of the marker, and correlating the position of the marker with the position of the CTV. Similarly, the uncertainties in targeting are divided into those related to the instantaneous targeting, and those from the latency. The uncertainties in instantaneous targeting include the accuracy of the machine and the residual motion. In total, the lowest level of the uncertainty tree has six leaves related to treating a moving CTV. These are described individually below.

1. Instantaneous measurement of position: This uncertainty results from the accuracy of which a static measurement of position can be made.

2. Correlation between marker and CTV positions: The measurement of position is not necessarily of the CTV itself. Rather, it may be of an internal or external marker. This uncertainty accounts for the imperfect correlation between the position of the marker and the position of the CTV.

3. Prediction of position in between measurements: For occasional measurements, the position between measurements may be unknown and may be predicted. This uncertainty accounts for the differences between actual and predicted positions.

4. Machine accuracy: This uncertainty describes the accuracy that the treatment machine can hit a target at a known position and time.

5. Residual motion: For gated treatments, the beam may be on for a range of target positions. This range may be considered an uncertainty, since the actual instantaneous position may be anywhere within the window of pre-defined range.

6. Latency: The position at a particular time is measured, and the radiation may be delivered at a later time. The change in position between the two times may be expressed as an uncertainty. This example of latency includes all its components, including the latency due to the measurement of position and the latency due to moving the linac or MLCs.

4. Motion Traces

Also, in the illustrated examples, ten patient motion traces are analyzed to illustrate the utility and effect of the inventive method. The traces are for motion in the thorax in the superior-inferior direction, and the entire trace (spanning 45-90 s) is used. Traces may be manually digitized using computer monitor and mouse (or may be automatically digitized using a processing unit), and interpolated between digitized points to create position values every 10 ms. The coordinate system is defined such that the end-of-exhale position is more negative than the end-of-inhale position and the time-averaged position is zero. The coordinate system may be arbitrarily defined in other manners in other embodiments.

In the motion traces illustrated in FIGS. 5A-5D, positions of vascular structures in the lungs of healthy volunteers were measured using cine-MRI with a frame rate of 4 Hz. The volunteer was instructed to perform both regular and irregular breathing. Four traces from the same volunteer, presented in FIGS. 5A-5D, are used.

The next four traces shown in FIGS. 5E-5H are position data obtained from patients treated with a radiation system. The position of the chest wall was monitored at 32 Hz by using light emitting diodes attached to the chest. Orthogonal kV images were acquired on a period of ~30 s. The lesion position was inferred from the position of the external marker, using an internal/external correlation model updated as new kV images were acquired.

Figure 5:
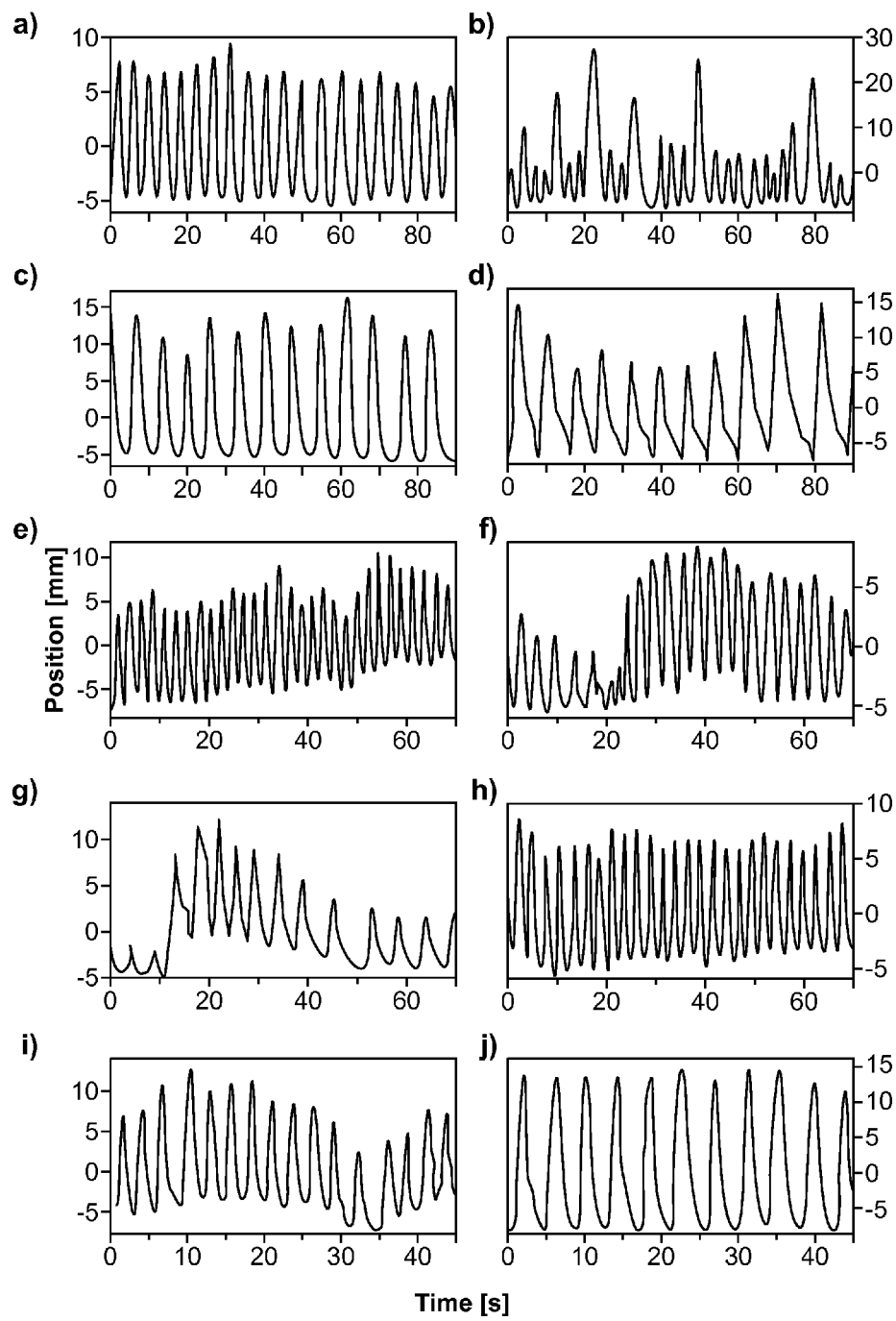
FIG. 5 illustrates examples of motion traces.

In the motion traces shown in FIGS. 5I-5J, the positions of the diaphragm are obtained using fluoroscopy. The diaphragm position was used to approximate the lesion position. For the purposes of discussion with respect to the illustrated method, the diaphragm position may be considered to be equivalent to the lesion position, and the CTV position. Two traces were obtained, for the same patient. During acquisition of the trace in FIG. 5I, the patient was undergoing free breathing, and during acquisition of the trace in FIG. 5J, the patient was undergoing verbally-coached breathing.

Characteristics of the traces of FIGS. 5A-5J are shown in FIG. 6. Over the 10 traces, the mean peak-to-peak and RMS amplitudes were 20.8 mm and 5.4 mm, respectively. The mean of the margins that would encompass 97.5% of the motion was 9.1 mm. The velocity at a given time was calculated as the average over 0.1 s. The mean of the maximum magnitudes of the velocities was 39.0 mm/s, and the mean of the RMS velocities was 9.7 mm/s.

It should be noted that a motion trace may be obtained in other manners in other embodiments. For example, in other embodiments, a motion trace may be obtained by recording the position of a marker block on the patient's chest over the same time period as the fluoroscopy, using the RPM system (Varian Medical Systems, Palo Alto Calif.). In further embodiments, a motion trace may be obtained by recording a position of an implant over a period of time. In some embodiments, the implant may be an active fiducial that emits a signal to indicate its position. In other embodiments, the implant may be a passive fiducial, such as a radio-opaque marker.

5. PDFs for the Respective Sources of Uncertainty

In the illustrated example, PDFs for the respective sources of uncertainty are determined. Each source of uncertainty may be initially considered independently. PDFs of the displacement between beam and lesion were created as described below, assuming other sources of uncertainty were negligible.

1. Instantaneous measurement of position: A PDF related to an uncertainty in hitting a target due to measurement of position may be determined. In some embodiments, electromagnetic beacon(s) implanted inside a patient may be used to determine a position of a target. In such cases, values for the uncertainty in the use of electromagnetic beacon(s) may be determined (e.g., measured, or obtained from a source such as a database or a medium that already stores such data). In one example, Calypso electromagnetic beacons (Varian Medical Systems, Palo Alto Calif.) may be used to measure positions. For one system, the differences between measurements of the positions of the beacons relative to the position of the detection array (for detecting or receiving signals from the beacon(s)), and the known positions, were found to be described by a mean of 0.4 mm and a standard deviation of 0.4 mm. This is conservatively approximated as a Gaussian distribution with standard deviation 0.8 mm centered on zero. It is assumed that the position of the detection array could be measured sufficiently accurately that the uncertainty is negligible compared to the uncertainty of measuring the beacon positions.

In other embodiments, the device for determining the position may be other types of devices. For example, in other embodiments, the device for determining position may be a camera that is configured to view one or more markers. The markers may be on a marker block, or may be coupled to the patient individually. In further embodiments, the markers may be landmarks on the patient.

In some embodiments, the information regarding the accuracy of position measurements (e.g., PDF for the position measurements) may be presented in a screen to a user, so that the user may use the information to perform treatment planning. For example, the information may be presented during a treatment planning session that occurs before a treatment session. In other embodiments, the information may be presented during a treatment session so that a treatment plan may be created (e.g., by modifying a previously determined treatment plan, etc.) during treatment. Also, in some embodiments, the information regarding the accuracy of position measurements may be stored in a non-transitory medium for later processing.

2. Correlation between marker and lesion positions: A PDF related to an uncertainty in hitting a target due to a correlation between marker and lesion positions may be determined. In some embodiments, two simultaneous motion traces of the lesion and an external marker may be analyzed using a processing unit. A model may then be created by the processing unit to relate the lesion position to the marker position. Motion traces may be first divided into inhale and exhale traces, based on the direction of motion of the marker. For each trace (of a given direction), a fourth-order polynomial may be fitted to the lesion position as a function of marker position. Treatment may be simulated by inferring the lesion position from the marker position using an appropriate fit function. The uncertainty PDF may calculated using the processing unit from the differences between the inferred and measured lesion positions over the time period of the motion traces.

Figures 7A, 7B:
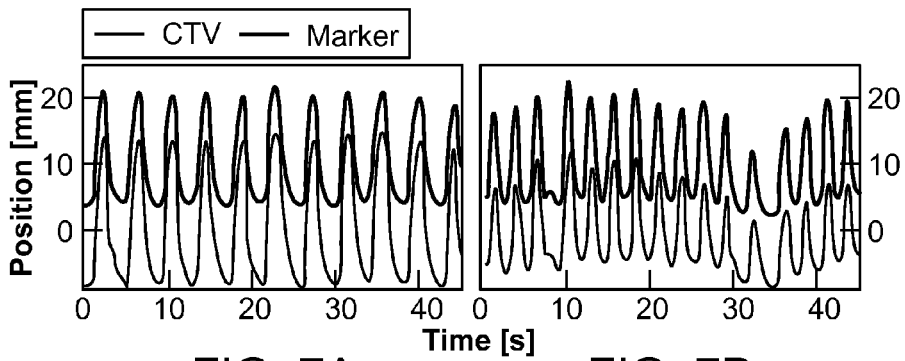
FIGS. 7A and 7B illustrate exemplary positions of a CTV and marker as function of time.
Figures 7C, 7D:
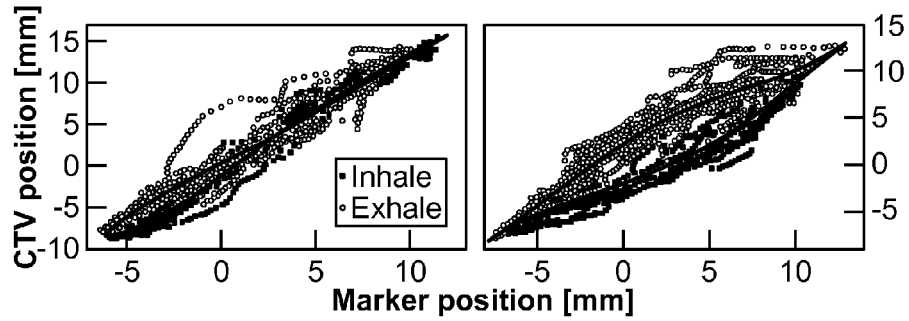
FIGS. 7C and 7D show exemplary CTV position as a function of marker position.
Figures 7E, 7F:
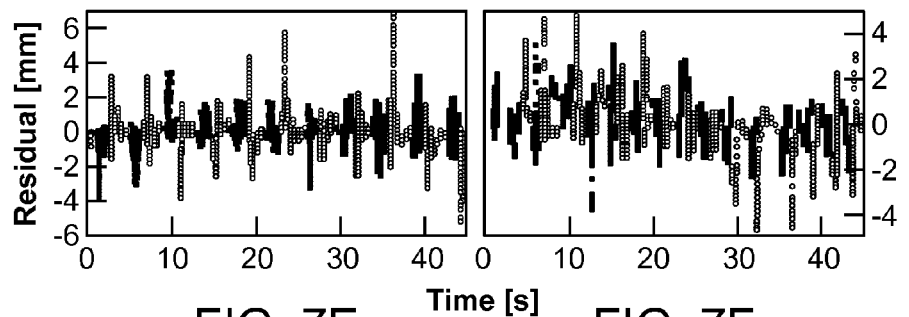
FIGS. 7E and 7F show exemplary residuals.
Figures 7G, 7H:
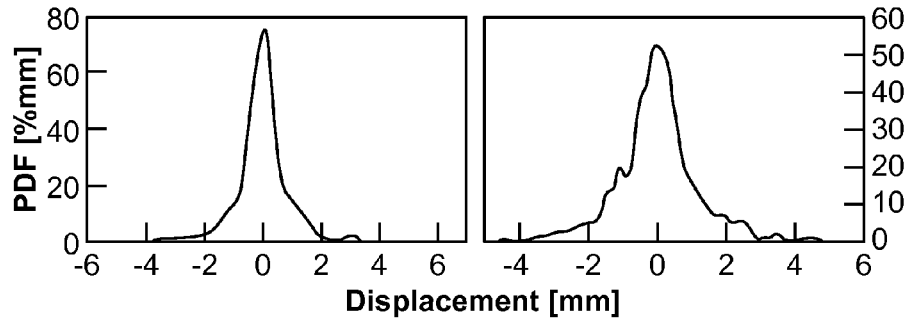
FIGS. 7G and 7H show exemplary PDFs constructed from the residuals.

In one example shown in FIG. 7A, simultaneous traces of the marker and CTV were processed. During acquisition of the data in FIG. 7A, breathing was coached; during acquisition of the data in FIG. 7B, the patient was free breathing. FIGS. 7C and 7D are plots of marker position versus CTV position. The data points were divided into inhale and exhale. Hysteresis was evident near the end-of-exhale position, while breathing was coached, and over the full trace, while free breathing. The polynomial fits to the data are shown. The residuals between the inferred and the measured CTV positions as a function of time are shown in FIGS. 7E and 7F. For coached breathing, most of the points were within 1 mm of zero, but there were occasional spikes of up to 7 mm magnitude. These typically occurred right at the transition between inhale and exhale, or vice versa. For some transitions, the marker began to move either before or after the diaphragm. While free breathing, there was an additional variation in the baseline of ±1 mm that correlated with the baseline drift in the motion trace. The PDFs constructed from the residuals using a processing unit are shown in FIGS. 7G and 7H. The margin required to account for the imperfect correlation between measured and inferred CTV positions was 3.0 mm for coached breathing and 3.3 mm for free breathing. In some embodiments, such values may be determined manually by visual review. In other embodiments, such values may be determined automatically by the processing unit.

In some embodiments, any or a combination of the plots shown in FIG. 7 may be presented in a screen to a user, so that the user may use the information to perform treatment planning. For example, the information may be presented during a treatment planning session that occurs before a treatment session. In other embodiments, the information may be presented during a treatment session so that a treatment plan may be created (e.g., by modifying a previously determined treatment plan, etc.) during treatment. Also, in some embodiments, any or a combination of the information shown in the plots in FIG. 7 may be stored in a non-transitory medium for later processing.

3. Prediction of position between measurements of positions: A PDF related to an uncertainty in hitting a target due to a prediction of position between position measurements may be determined. In some embodiments, a virtual set of measurement data may be created by extracting positions determined at a given measurement frequency from the motion trace. These positions represent the results of the measurements of position. A prediction function may be fitted to a subset of the virtual measurement data, and may be used to predict the position between the last measurement in the subset, and the next virtual measurement. The length of time over which the fit is made may be denoted the fit interval. In some embodiments, a sine function may be used by the processing unit as the prediction function. In other embodiments, other functions may be used. Each fit may be offset such that the fit function coincides with the last data point in the subset of virtual measurements. A PDF may be formed by the processing unit from the differences between predicted and actual positions at times between measurements over the motion trace.

Figure 8:
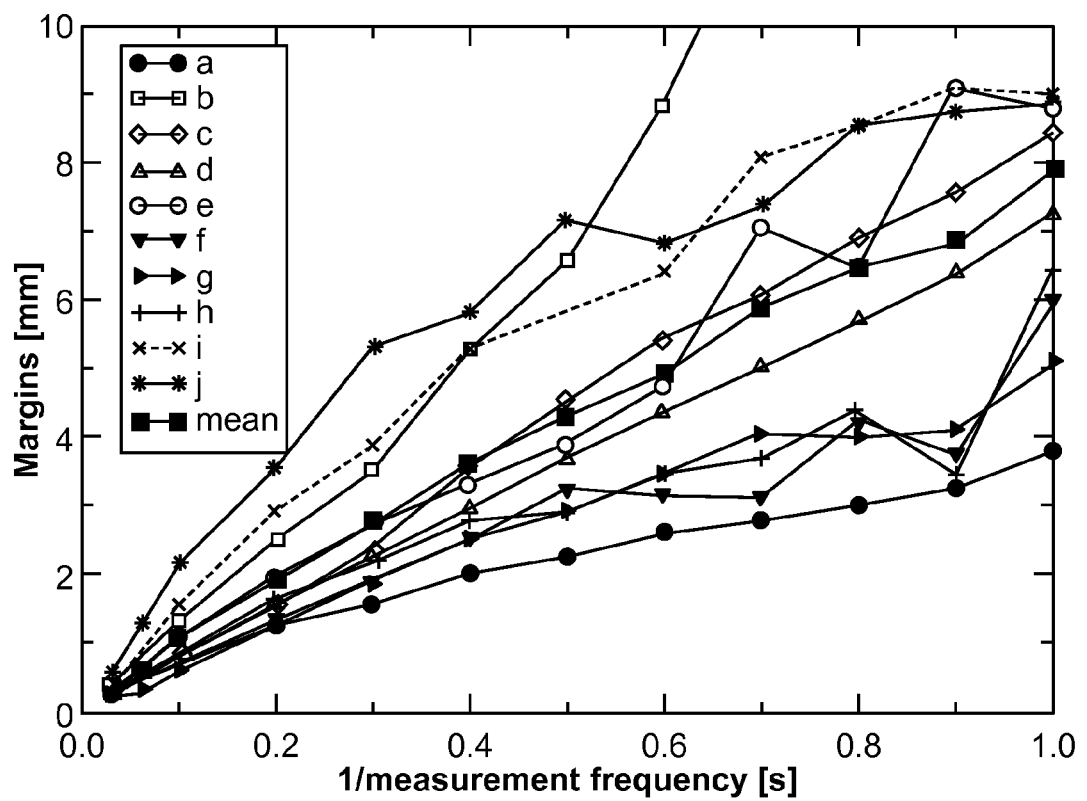
FIG. 8 illustrates examples of margins for different motion traces.

In one example, measurement frequencies from 1 Hz to 33 Hz were considered. Fit intervals in the range of 1 s to 10 s were considered. For each measurement frequency and motion trace, the fit interval that resulted in the lowest margin was used. Margins required to account for the change of CTV position between measurements are shown in FIG. 8 for the 10 motion traces. Margins are plotted against the inverse of measurement frequency. For high measurement frequencies, the margins approached zero. On decreasing the measurement frequency, the margins increased nearly linearly with the measurement period. The rate of increase was different for each motion trace, and ranged from 5 to 18 mm/s. The mean margins were described by a line with slope 8.7 mm/s. At measurement frequencies of 2 Hz (16 Hz), the mean margins were 4.3 (0.6) mm, respectively. The minimum and maximum margins for the individual traces at those measurement frequencies were 2.3 (0.3) and 7.2 (1.3) mm, respectively.

The traces that were outliers were characterized by similar features. Motion traces that required the largest margins included (i), (j), and (b). The first two of these traces were regular, but showed a large asymmetry between inhale and exhale. The prediction algorithm was therefore not able to accurately predict the position of an inhale peak, say, based on the position of the previous end-of-exhale peak. Trace (b) had highly inconsistent breathing amplitudes. The prediction algorithm predicted one breathing cycle to be similar to the previous one, and therefore did poorly when the amplitudes varied. Motion traces that were predicted well were symmetric with regard to inhale/exhale, and had consistent amplitude from cycle to cycle. Examples of such were traces (a) and (f).

In some embodiments, the plot shown in FIG. 8 may be presented in a screen to a user, so that the user may use the information to perform treatment planning. For example, the information may be presented during a treatment planning session that occurs before a treatment session. In other embodiments, the information may be presented during a treatment session so that a treatment plan may be created (e.g., by modifying a previously determined treatment plan, etc.) during treatment. Also, in some embodiments, the information shown in the plot in FIG. 8 may be stored in a non-transitory medium for later processing.

4. Machine accuracy: A PDF related to an uncertainty in hitting a target due to machine accuracy may be determined. The end-to-end accuracy of a radiation treatment system may be obtained from publication, and be converted to a PDF using a processing unit. In other embodiments, the accuracy of a radiation system may be measured. For example, data from a simulation or data from an actual treatment session may be obtained by a processing unit. The processing unit may then process the data to create the PDF.

In one example, the end-to-end targeting accuracy of a dose delivery was determined by delivering dose to a phantom with embedded film. For nine treatment plans they found that the maximum magnitude of geometric displacement in three dimensions between the measured dose and the planned dose was <0.9 mm. With the assumptions that this value represented the $2\sigma$ value of a Gaussian distribution, and that the targeting uncertainty could be divided into uncertainties for two orthogonal directions, the machine accuracy was given by a Gaussian with $\sigma$=0.3 mm. This was a conservative estimate, because the end-to-end test included more sources of uncertainty than machine accuracy.

In some embodiments, the information regarding the machine accuracy (e.g., PDF for the machine accuracy) may be presented in a screen to a user, so that the user may use the information to perform treatment planning. For example, the information may be presented during a treatment planning session that occurs before a treatment session. In other embodiments, the information may be presented during a treatment session so that a treatment plan may be created (e.g., by modifying a previously determined treatment plan, etc.) during treatment. Also, in some embodiments, the information regarding the machine accuracy may be stored in a non-transitory medium for later processing.

5. Residual motion: A PDF related to an uncertainty in hitting a target due to residual motion may be determined. In some embodiments, the uncertainty from residual motion may be a function of the duty cycle. For a given duty cycle, the motion margin may be defined as the minimum range of allowed motion such that a desired duty cycle is obtained. The duty cycle for each motion margin may be calculated using the processing unit by considering each point in the motion PDF as a reference point. Motion margins about the reference points may be defined, and the duty cycle for each reference point may be calculated by the processing unit. For a particular motion margin, the maximum of all the duty cycles for the different reference points may be chosen as the duty cycle.

In one example, baseline correction was applied to a set of motion traces. The baseline correction allows the relation between duty cycle and motion margin to be better defined in the presence of baseline drift. Between each pair of end-of-exhale positions, the baseline was determined as the line containing the previous two end-of-exhale positions. The baseline was subtracted from the position data. End-of-exhale positions were determined as the positions in the motion trace that were more negative than in the following or preceding 1 s.

Figure 9:
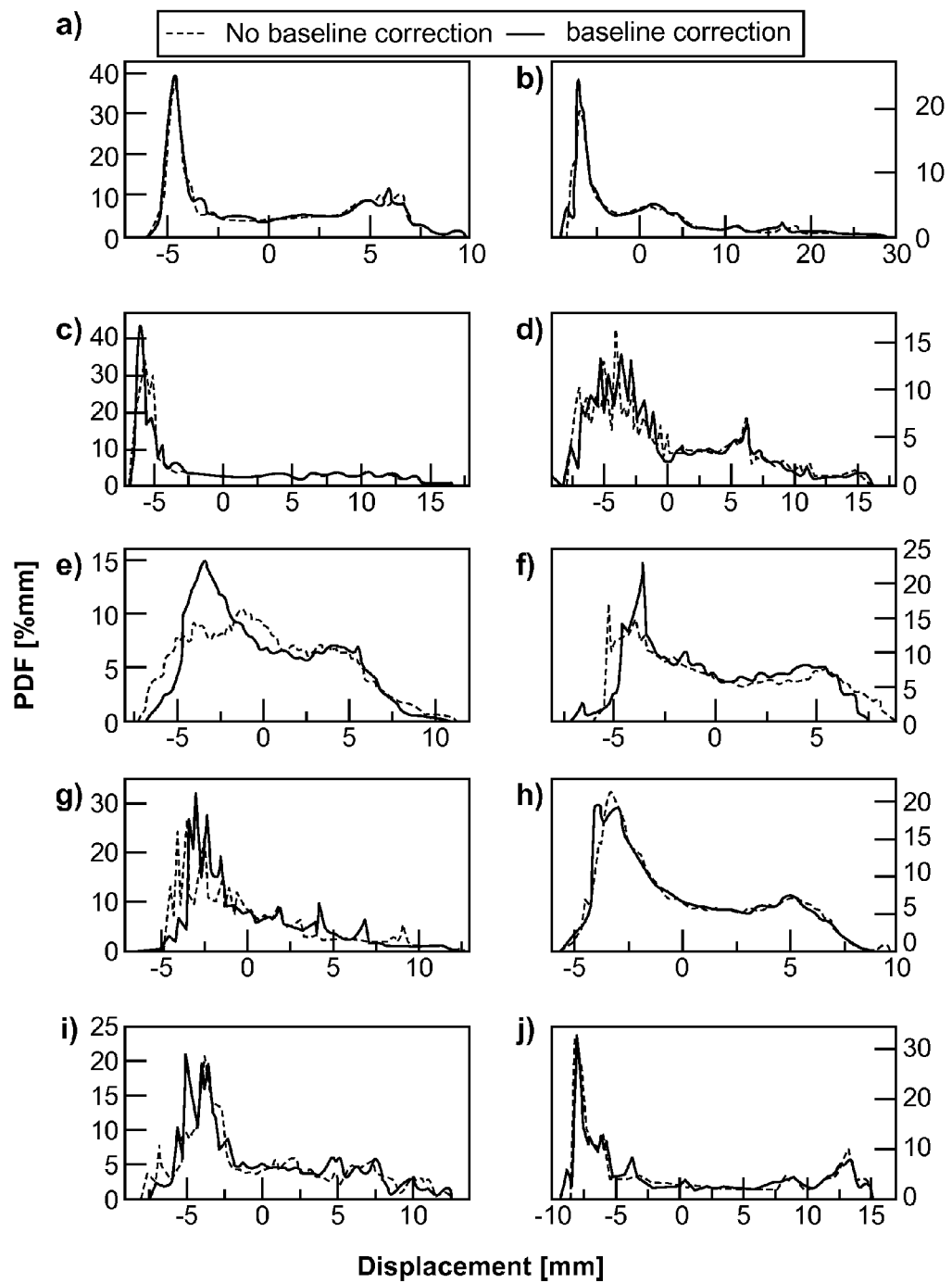
FIG. 9 illustrates examples of PDFs of motion traces.

In one example, the PDFs of the CTV positions for the 10 traces are shown in FIG. 9, with and without baseline correction. Consider first the PDFs with no baseline correction. Most of the PDFs were characterized by a large peak at the end-of-exhale position. The amplitude of the peak varied, and was a maximum of 40 %/mm for trace (a). Several of the traces also showed a smaller peak at the inhale position. The shapes of the peaks varied, and for several traces there were multiple peaks at end-of-exhale. Trace (e), which showed a pronounced baseline drift in the motion trace, was alone in not showing an end-of-exhale peak. After correcting for baseline drift, most PDFs (shown in red) were largely unchanged. The exception was trace (e), for which end-of-exhale and end-of-inhale peaks were visible in the PDF only after baseline correction.

Figure 10:
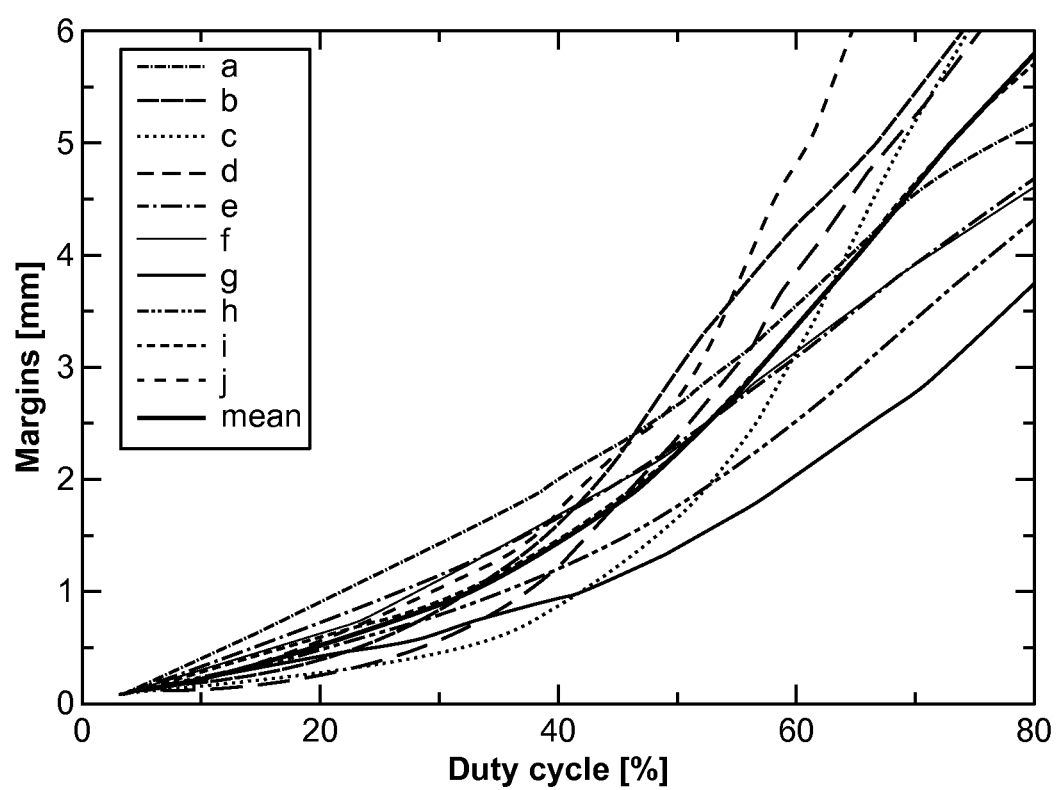
FIG. 10 illustrates examples of margins as a function of duty cycle for a gated treatment.

The required margins due to residual motion for the 10 baseline-corrected motion traces are shown in FIG. 10 as a function of duty cycle. For duty cycles below 30-40%, margins were proportional to the duty cycle. The constant of proportionality ranged from 0.01 to 0.045 mm/%, with mean 0.025 mm/%. For duty cycles above 40-50%, the relation between margin and duty cycle was linear, with slopes in the range 0.08 to 0.24 mm/%, and mean 0.12 mm/%. At a duty cycle of 33%, the margins ranged from 0.6 to 1.6 mm, with a mean of 1.0 mm. At a duty cycle of 50%, the margins ranged from 1.4 to 3.0 mm, with mean 2.3 mm. At low duty cycles, the outlier with highest margins was (d). This trace was characterized by a constantly moving CTV at exhale. The end-of-exhale peak in the PDF, and therefore the margin, was wide. The motion traces with the narrowest margins were (a) and (c). These traces had consistent end-of-exhale positions during which the CTV was stationary, and large amplitude, narrow peaks in the motion PDFs at end-of-exhale. At high duty cycles, (g) had narrow margins compared to the other traces. This motion trace was inconsistent, but showed both long times at the end-of-exhale position and a small breathing amplitude.

In some embodiments, the information regarding the residual motion (e.g., PDF of motion traces, duty cycles-vs-margins plot, etc.) may be presented in a screen to a user, so that the user may use the information to perform treatment planning. For example, the information may be presented during a treatment planning session that occurs before a treatment session. In other embodiments, the information may be presented during a treatment session so that a treatment plan may be created (e.g., by modifying a previously determined treatment plan, etc.) during treatment. Also, in some embodiments, the information regarding the residual motion may be stored in a non-transitory medium for later processing.

6. Latency: A PDF related to an uncertainty in hitting a target due to latency may be determined. The latency $T_L$ may be defined as the difference between the time at which position was measured and the time at which radiation could be delivered based on that measurement. The uncertainty PDF may be formed using the processing unit from the differences of target positions at times t and $t+T_L$ over the motion trace. Latencies from 0.05 s to 0.5 s may be considered in some embodiments. Latencies with other ranges of time may be considered in other embodiments.

Figure 11:
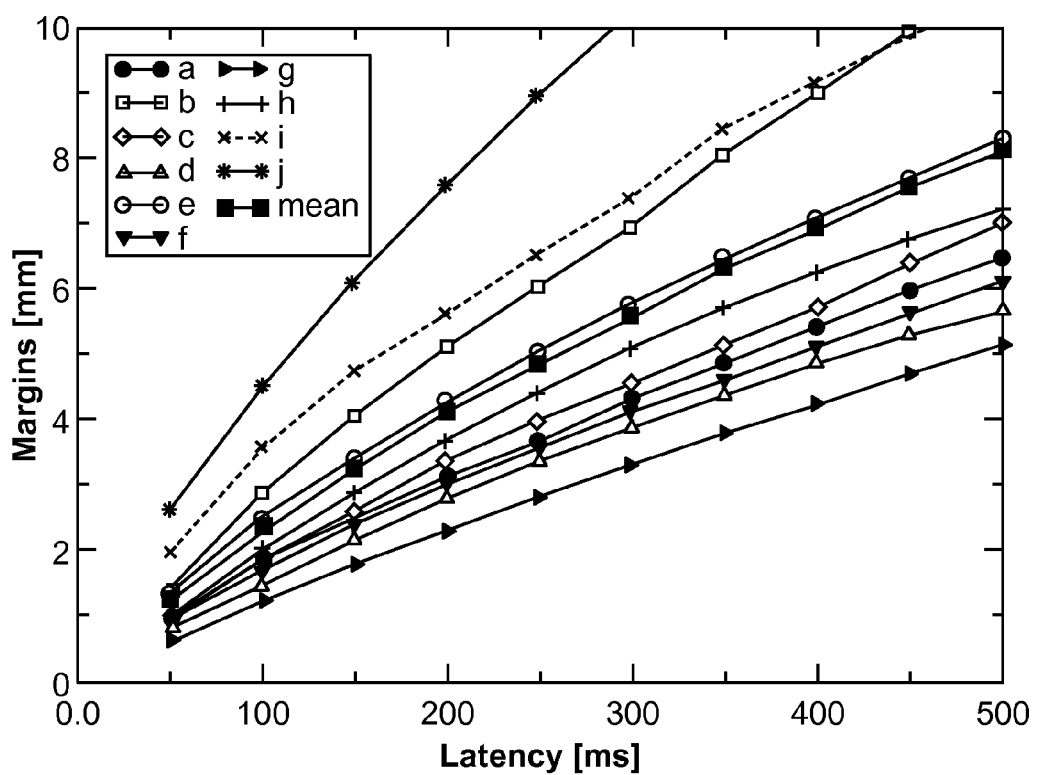
FIG. 11 illustrates examples of margins as a function of latency.

In one example, margins resulting from latency for the 10 motion traces are shown in FIG. 11 for latencies in the range 0.05 s to 0.5 s. For small latencies, the margins may be proportional to the latency. The slopes ranged from 13 mm/s to 45 mm/s, with mean 24 mm/s. There curves flattened slightly at latencies approaching 0.5 s. At a latency of 0.05 (0.2) s, the margins had mean values of 1.2 mm (4.1 mm), and ranged from 0.6 to 2.6 mm (2.3 to 7.6 mm). Motion traces which were outliers had similar features. The traces with the largest margins were (i), (j), and (b). These traces all had the largest maximum and RMS velocities. The former two traces had long times at end-of-exhale, relative to the breathing period, and large amplitudes of motion, resulting in large velocities. The latter trace had occasional large amplitude inhalations, during which the lesion moved rapidly. The trace with the smallest margins, (g), had the smallest RMS velocity, and nearly the smallest maximum velocity. It also had a small breathing amplitude, and long periods of time at end-of-exhale.

In some embodiments, the information regarding the latency (e.g., PDF for the latency, latency-vs-margins plot, etc.) may be presented in a screen to a user, so that the user may use the information to perform treatment planning. For example, the information may be presented during a treatment planning session that occurs before a treatment session. In other embodiments, the information may be presented during a treatment session so that a treatment plan may be created (e.g., by modifying a previously determined treatment plan, etc.) during treatment. Also, in some embodiments, the information regarding the latency may be stored in a non-transitory medium for later processing.

6. Combining PDFs

In the exemplary method, after the PDFs have been determined, the PDFs may be combined to consider the effect of the combined uncertainties (like item 266 discussed with reference to the method 260 of FIG. 2). In the illustrated example, individual sources of uncertainty are combined to form the positional uncertainty for different motion management strategies. PDFs are combined by convolution in the illustrated embodiments. Convolution may be performed using multiplication, addition, integration, etc., or combination of the foregoing.

Motion margins may be calculated from the requirement that the minimum dose to the CTV be 95% of the prescription dose. Neglecting scatter, this is equivalent to requiring that the reference point of the CTV be within the margin of the reference point of the radiation beam 95% of the time. It is assumed that there is motion in two orthogonal directions contributing to the margins. In other embodiments, motion in other orthogonal direction(s) may be considered. Also, in other embodiments, the value may be different from 95% (e.g., higher or lower than 95%). For simplicity, it may be assumed that for each direction, the reference point of the CTV is required to be within the margin of the reference point of the radiation beam $(0.95)^{1/2}=0.975$ of the treatment time. The motion margin is the minimum value encompassing 97.5% of the area of the PDF, and may be determined by numerical integration using a processing unit.

In the illustrated examples, the uncertainties are combined for different motion management strategies. Five exemplary motion management scenarios are considered, as described below.

1. Tracking with Latency of 200 ms

In this first motion management/treatment strategy, suppose that the patient has electromagnetic beacons implanted internally, and that the correlations between the CTV positions and those inferred from the beacons can be described as a delta function. There is no residual motion, because this is not a gating strategy. Suppose that the latency is 200 ms. For each trace, the combined uncertainty is the convolution of the uncertainty for measurement accuracy, prediction, machine accuracy, and latency. The convolution may be achieved using the processing unit, which performs calculation to combine the different PDFs.

The processing unit calculated motion margins from the resultant motion PDF, wherein the motion margins are shown in FIG. 12A for each motion trace. In some embodiments, the graph of FIG. 12A may be provided using the processing unit and may be presented on a screen for allowing a user to examine the result of the analysis provided by the processing unit. For example, from the graph, the user may see that at high measurement frequencies, the margins reached a plateau at non-zero values. Also, from the graph, the user may see that the values ranged from 3.0 to 8.0 mm, and had a mean value of 4.6 mm. These values were within 0.7 mm of the values solely resulting from the latency of 200 ms (FIG. 11). As the measurement frequency decreased, the margins at first were nearly constant then began to increase near 10 Hz. At a measurement frequency of 2 Hz, the margins ranged from 3.9 to 10.0 mm, and had a mean value of 6.1 mm. At 1 Hz, the mean of the motion margins was 9.3 mm.

In some embodiments, the processing unit may be configured to determine motion margins based on the requirement that the minimum dose to the CTV be 95% of the prescription dose, or that the reference point of the CTV be within the margin of the reference point of the radiation beam 95% of the time. It may be assumed that there is motion in two orthogonal directions contributing to the margins. In other embodiments, motion in other orthogonal direction(s) may be considered. Also, in other embodiments, the value may be different from 95% (e.g., higher or lower than 95%). For simplicity, it may be assumed that for each direction, the reference point of the CTV is required to be within the margin of the reference point of the radiation beam $(0.95)^{1/2}=0.975$ of the treatment time. The motion margin is the minimum value encompassing 97.5% of the area of the PDF, and may be determined by numerical integration using the processing unit. In some embodiments, the required motion margin may be entered into the processing unit as an optimization variable for use in an optimization algorithm.

2. Tracking with Latency of 100 ms

In this second motion management/treatment strategy, suppose that the same tracking strategy as above is applied, but with a latency of 100 ms. Motion margins are calculated again using the processing unit, and are shown in FIG. 12B. In some embodiments, the graph of FIG. 12B may be provided using the processing unit and may be presented on a screen for allowing a user to examine the result of the analysis provided by the processing unit. For example, from the graph, the user may see that at high measurement frequencies, the motion margins for each trace ranged from 2.2 to 4.9 mm, and had a mean of 3.1 mm. Motion margins increased as the measurement frequency decreased. At 2 Hz, the mean of the motion margins was 5.2 mm, and at 1 Hz the mean was 8.6 mm.

3. Gating with an Internal Marker, 33% Duty Cycle, and Latency of 100 ms

In this third motion management/treatment strategy, consider a gating strategy with an implanted marker (e.g., beacon). Suppose that the latency is 100 ms, lower than that for tracking because the linac is not required to move. A duty cycle of 33% with baseline subtraction is used. The uncertainty is the convolution of the individual uncertainties for measurement accuracy, prediction, latency, machine accuracy, and residual motion.

Motion margins are calculated again using the processing unit, and are shown in FIG. 12C for each motion trace. In some embodiments, the graph of FIG. 12C may be provided using the processing unit and may be presented on a screen for allowing a user to examine the result of the analysis provided by the processing unit. For example, from the graph, the user may see that for a measurement frequency of 33 Hz, the margins for each trace had non-zero values ranging from 2.4 to 5.2 mm, with mean 3.4 mm. The mean value was 1 mm greater than that for a latency of 100 ms considered in isolation. On decreasing the measurement frequency, the motion margins were nearly constant until 10 Hz. At lower frequencies the motion margins increased. At a measurement frequency of 2 Hz the motion margins ranged from 3.5 to 8.3 mm, with mean 5.4 mm. At 1 Hz, the mean of the motion margins was 8.7 mm.

4. Gating with an External Marker, Duty Cycle 33%, and Negligible Latency

In this fourth motion management/treatment strategy, suppose that a gating strategy is used with an external marker. The latency results from measuring the position of the external marker, and holding the beam. A duty cycle of 33% with baseline correction is used. The uncertainty is the convolution of the uncertainties in measurement accuracy, prediction, machine accuracy, residual motion, and correlation. In some cases, a correlation PDF for a trace may be taken to be representative, and be used for all traces. This may be helpful especially when correlations are not available for all of the motion traces.

The resulting motion PDFs led to motion margins shown in FIG. 12D. In some embodiments, the graph of FIG. 12D may be provided using the processing unit and may be presented on a screen for allowing a user to examine the result of the analysis provided by the processing unit. For example, from the graph, the user may see that for high measurement frequencies the motion margins clustered at a mean value of 3.2 mm. The minimum and maximum values were 3.1 and 3.4 mm, respectively. On decreasing the measurement frequency, the motion margins first remained nearly constant, then at a measurement frequency near 5-10 Hz the motion margins increased. At measurement frequencies of 2 and 1 Hz, the means of the motion margins were 5.3 and 8.6 mm, respectively.

5. Gating with an Internal Marker and a 50% Duty Cycle

In this fifth motion management/treatment strategy, consider gating with an internal marker (like motion management strategy No. 3), but with an increased duty cycle of 50%, and the motion margins were increased (shown in FIG. 12E). In some embodiments, the graph of FIG. 12E may be provided using the processing unit and may be presented on a screen for allowing a user to examine the result of the analysis provided by the processing unit. For example, from the graph, the user may see that at high measurement frequencies, the motion margins ranged from 2.8 to 5.7 mm, with a mean of 4.0 mm. At measurement frequencies of 2 and 1 Hz, the means of the motion margins were 5.7 and 9.0 mm, respectively.

Figure 13:
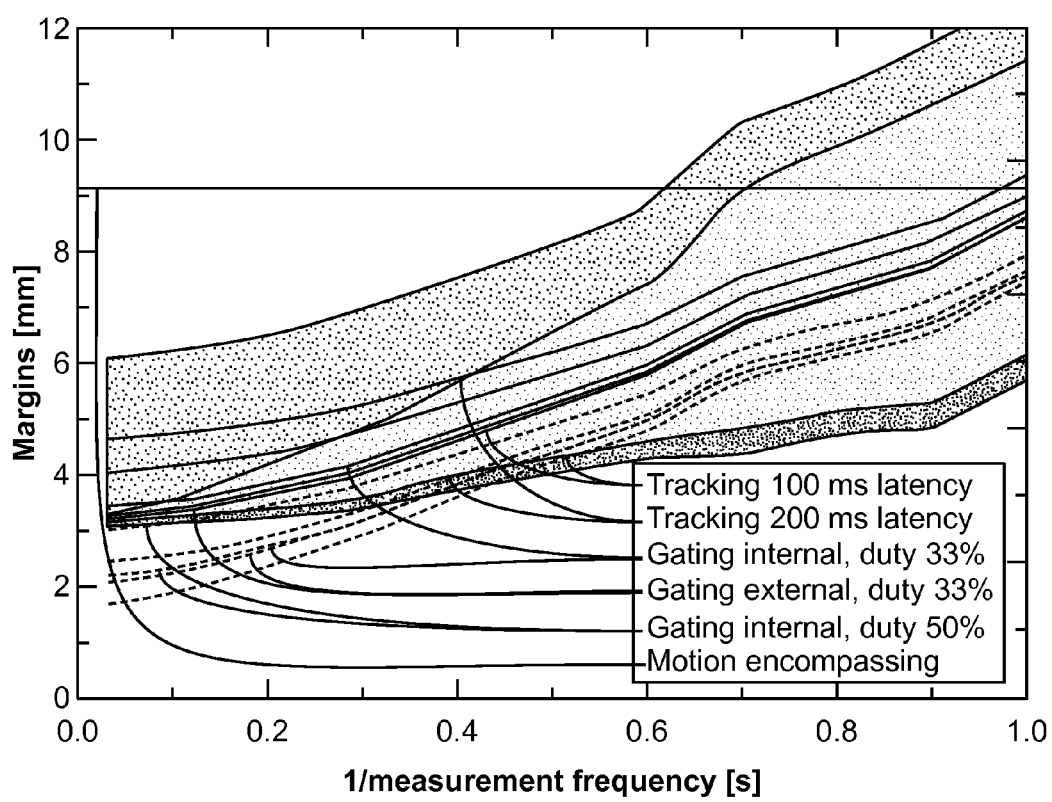
FIG. 13 illustrates a comparison of the means of the margins for the different treatment strategies.

In some embodiments, a user interface may be presented on a screen for displaying PDFs convolution results and related information for different respective motion management strategies, so that a technician may evaluate and compare the different motion management strategies. For example, following the above examples, the mean motion margins for the five motion management strategies considered above may be plotted as lines and be displayed in a screen (FIG. 13). The motion margins for the gating strategies with a duty cycle of 33%, with either the external or internal marker, were similar to those for tracking with a 100 ms latency over the 30 range of measurement frequencies. The mean of the motion margins was 3 mm at a measurement frequency of 33 Hz. For tracking with a latency of 200 ms, the mean motion margin was 4.6 mm at 33 Hz. For internal gating with a duty cycle of 50%, the motion margin were 4.0 mm at 33 Hz. These values were intermediate between those for tracking with a latency of 200 ms, and those for either tracking with a latency of 100 ms or either gating strategy with a duty cycle of 33%. At 1 Hz all the strategies required motion margins near 9 mm.

In some embodiments, the above motion margins calculated by the processing unit may be summarized in a chart shown in FIG. 13, and may be presented to a user to assist the user in making motion management decision. These motion margins at measurement frequencies greater than 1 Hz were lower than those for a motion-encompassing strategy. At a minimum, motion-encompassing margins need to account for the motion of the CTV during the motion trace. Averaged over the 10 traces, the margin required such that the CTV was in the beam 97.5% of the time was 9.1 mm. This value is shown as a horizontal line in FIG. 13. It intersects the curves for the various motion management strategies near a measurement frequency of 1 Hz. At 33 Hz, the motion-encompassing margins are 2-3 times those for the various motion management strategies.

The standard deviations of the distributions of motion margins for the ten traces are shown as shaded areas, for tracking with latency of 100 ms and gating with an external marker. The standard deviation for the external gating strategy was low at high measurement frequencies, because the same correlation uncertainty was used for each trace. The difference between the mean motion margins for the different strategies at a measurement frequency of 33 Hz was one standard deviation of the tracking results. At 1 Hz, the differences in mean motion margins for the different strategies were much less than one standard deviation.

The curves representing the mean motion margins can be characterized. At high measurement frequencies, latency was a dominant source of uncertainty. For tracking with a latency of 200 ms, almost all of the motion margins resulted from latency. On reducing the latency to 100 ms, other sources of uncertainty such as the measurement accuracy and, for gating, the residual motion and the correlation between internal and external positions, become important. As the measurement frequency was reduced, the prediction uncertainty became more important. At 1 Hz it was the dominant source of uncertainty.

As illustrated in the above examples, five motion management strategies were compared by dividing the uncertainty in targeting accuracy into its components. Mean margins required to account for the center of mass motion of the CTV were determined. At high measurement frequencies, tracking with a latency of 100 ms was found to require the narrowest motion margins, of 3.1 mm, and tracking with a latency of 200 ms required the largest motion margins, of 4.6 mm. Gating with a duty cycle of 33%, and using either an internal or external marker required motion margins of 3.3±0.1 mm. With a duty cycle of 50%, the value for internal gating increased to 4.0 mm. These values were less than the 9.1 mm required to account for the motion of the CTV with a motion-encompassing strategy. At a measurement frequency of 1 Hz, motion margins required for all the strategies were near 9 mm.

It should be noted that the above five motion management scenarios are exemplary scenarios, and that in other embodiments, a motion management scenario may have characteristics (e.g., latency value, duty cycle, etc.) that are different from those discussed.

In some embodiments, the information provided by the processing unit may be viewed by a user on a screen, and the user may then decide on how the margins may be improved. Also, in some embodiments, the processing unit may be configured to provide recommendation on how to improve the margins, as well as calculating the amount of improvement based on the recommendation. For example, in some embodiments, the processing unit may be configured to determine improved PDFs of the individual sources of uncertainty, and to combine the improved PDFs to determine the required motion margins after reducing the individual sources of uncertainty.

In some embodiments, the margins may be improved based on one or more of the following: (1) reducing uncertainty from (or associated with) latency, (2) better prediction between measurements, (3) better correlation model, (4) reducing residual motion, and (5) improving position measurement accuracy. Each of these will be discussed below.

1. Reducing Uncertainty from Latency

In some embodiments, the margins may be improved by reducing uncertainty from latency or uncertainty associated with latency. Several techniques may be employed to reduce the uncertainty due to latency in different embodiments. For example, in some embodiments, a system latency may be reduced. In some cases, the manufacturer of the system may design the system with a certain prescribed latency. Reductions in motion margins due to latency may be determined from the information in FIG. 11.

In other embodiments, the position of tissue/marker at the end of the latency period may be predicted. In the above analysis, the change in position over the latency time was considered as the uncertainty. However, this uncertainty may be reduced if the position was predicted. To set a bound for this value, positions after the latency period were predicted using the algorithm described above for predictions between measurement points. For a latency of 200 ms, the margins required due to differences between actual and predicted positions, averaged over the 10 motion traces, were 3.0 mm, a 28% improvement over the value without prediction.

In other embodiments, the uncertainty due to latency may be reduced by using a more accurate prediction algorithm for predicting positions. In some embodiments, adaptive neural networks and linear adaptive filtering may be used to predict the position of an external marker. In other embodiments, sinusoidal prediction and an adaptive filter may be used. In some cases, a better prediction algorithm may provide a 10% improvement in reducing the PDF width. In some embodiments, the prediction algorithm is based on measured positions as a function of time. In other embodiments, the prediction algorithm may consider other information, such as velocity, to provide a more accurate prediction.

In some cases, a sine fit may not performed as well at transitions between inhale and exhale, and vice versa. Thus, it may be possible to reduce the residuals at these points. Possibilities include using a better prediction algorithm, reducing dose rate at these times, coaching the patient in breathing patterns, or obtaining a signal from the patient.

In some embodiments, the reduction in the width of the PDF may be 30% due to predicting the lesion position with a sine function, 10% from use of a better prediction algorithm, and 10% for other improvements, to achieve a 50% improvement.

2. Better Prediction Between Measurements

At low measurement frequencies, much of the motion margin may be resulted from predicting positions in between measurements. Improvements in prediction are similar to those discussed above in the context of latency.

3. Better Correlation Model

In treatments where the position of an external marker is measured, an improvement in the model relating the position of the marker to the position of the CTV may reduce the motion margins. The correlation model may produce large differences between measured and inferred CTV positions at the transitions between inhale and exhale, and vice versa. These differences occurred when either the CTV or the marker began to move before the other. In some cases, the amount of improvement may be estimated by removing the spikes at the transitions of the difference plot in FIG. 7. For trace (j), the required margins were reduced to 1.4 mm, from 3.0 mm. As in the case of predictions, discussed above, this improvement may be implemented by use of a prediction algorithm capable of predicting the transitions, or a system of coaching or signaling which provides advance knowledge of the transitions, or holding the beam when the marker position approaches a transition. Combining monitoring the external marker with occasional measurements of an internal fiducial position might also reduce the correlation uncertainty. For example, in some embodiments, occasional kV imaging may be performed (e.g., to confirm and/or improve the correlation model).

4. Reduced Residual Motion

In other embodiments, the margins may be reduced by decreasing the duty cycle. In some cases, a decrease in the duty cycle with other parameters held constant may increase treatment time. As shown in FIG. 10, below a duty cycle of 33% the motion margins were proportional to the duty cycle. In other embodiments, the dose rate may be increased, for example by removing a flattening filter. Conversely, increasing the duty cycle may have a larger effect on the motion margins. The plot of mean margin versus duty cycle in FIG. 10 had a positive second derivative near a duty cycle of 40%. Increasing the duty cycle from 33% to 50% increased the mean margin from 1.0 mm to 2.3 mm. Thus, in some embodiments, a duty cycle of 33% appears to be a reasonable compromise.

5. Measurement Accuracy

The uncertainty associated with the measurement of position may be reduced by using a measurement device that is more accurate, and/or by improving the position calculation algorithm for the measurement device.

6. Combined Improvements

In some embodiments, the processing unit may be configured to provide an estimate of the reduction in motion margins that may be obtained by implementing one or more of the above improvements. The estimate may then be presented on a screen for presentation to a user. In the illustrated example, an estimation of the reduction in motion margins may be determined by the processing unit by scaling the previously determined individual PDFs by the improvement values (e.g., the percentages) discussed above. The same treatment options as those for the previously determined PDFs may be considered in determining the new PDFs for each trace. The processing unit may then determine the mean motion margins for the improved PDFs. Mean motion margins for the improved PDFs are lower than those obtained previously, and are plotted in dashed lines in FIG. 13. The previously determined PDFs are shown in solid lines in FIG. 13. In the illustrated example, at a measurement frequency of 33 Hz, the lowest motion margin was 1.7 mm, obtained with tracking with a latency of 100 ms. Gating based on an external marker required a motion margin of 2.2 mm, and gating with an internal marker and a latency of 100 ms required motion margins of 2.1 mm. Tracking with a latency of 200 ms had motion margins of 2.4 mm, and gating based on an internal marker with a duty cycle of 50% required a motion margin of 3.0 mm. The tracking strategies were improved by 50%, and the gating strategies by 33%. At a measurement frequency of 1 Hz, all the motion management strategies required motion margins between 7 and 8 mm.

As indicated in the above examples, at high measurement frequencies, latency may be an important source of uncertainty. It is larger than the positional uncertainty related to residual motion, and therefore gated strategies may require the same or narrower motion margins than tracking strategies. Thus, embodiments of the system and method described herein may provide information to indicate to a user the different contributions to the margins from the different respective sources of uncertainty. By comparing the different contributions quantitatively, the user may then decide on a motion management strategy to achieve a certain desired margin for a specific patient.

Also, as indicated in the above examples, improvements may be made to the individual sources of uncertainty. The effects of latency may be reduced by various techniques, such as, predicting the CTV position at the end of the latency period. These improvements may reduce the margins required to account for a given latency by 50%. In the above examples, tracking with a latency of 100 ms has the lowest motion margin, at 1.7 mm. The two tracking strategies, and the two gating strategies with duty cycles of 33%, would all require motion margins in the region 2.0±0.4 mm. Gating with a 50% duty cycle would require motion margins of 3.0 mm. Also following the above examples, for tracking strategies to have narrower motion margins than gating strategies, the latency may be reduced to below 150 ms. With a latency of 200 ms, the gating strategies had narrower margins. Even with the potential reductions in the effects of latency, the gating strategies with duty cycles of 33% had narrow margins than tracking. At latencies above 150 ms, gating strategies may require equal or narrower motion margins than tracking strategies.

Thus, the system and method described herein are advantageous because they provide information based on different sources of uncertainty for assisting a user to make decision of a motion management strategy. In some embodiments, the system and method described herein may be used to determine motion management strategy that is tailored to a particular patient's motion and a particular machine's delivery characteristics. Using the system and method described herein, a final decision for motion management strategy may be made by the clinician after evaluating the pros and cons of the various available approaches for each specific patient and treatment scenario. Also, the system and method described herein are advantageous because they assist a user to design treatment plans that provide a high probability of target coverage, while minimizing extraneous dose outside the target.

In some embodiments, a result (such as margins) of the convolution of different probability density functions may serve as a factor or a parameter in determining treatment strategy, such as whether to hypo or hyper fractionate, whether to perform arc or rapidarc therapy, etc.

Although the above embodiments have been described with reference to radiation treatment, in other embodiments, the system and method described herein may be applied for other types of treatment that may or may not involve radiation. For example, in other embodiments, the method 260 may be performed for a proton treatment planning, or planning of other treatments that use heavy ions.

Computer System Architecture

Figure 14:
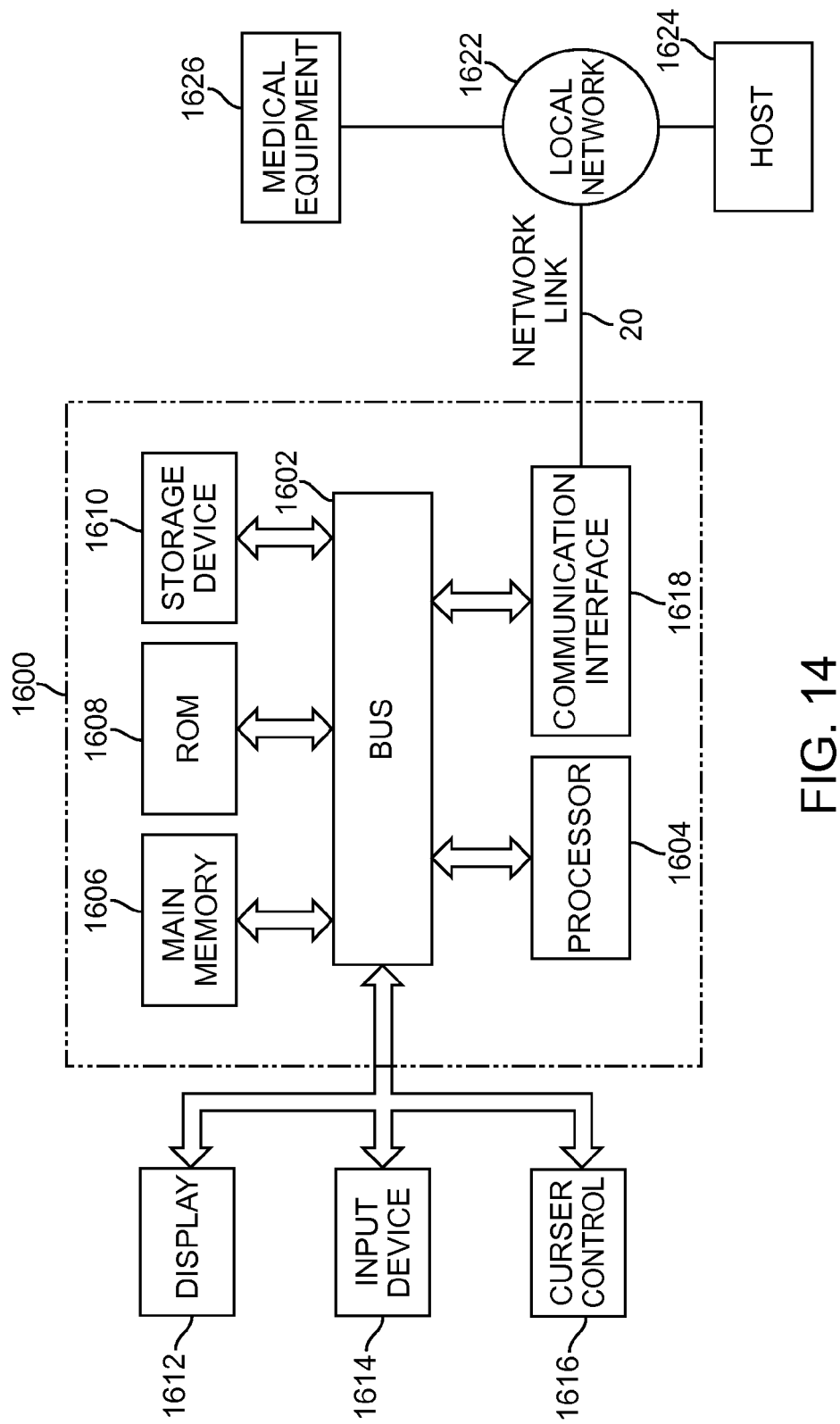
FIG. 14 illustrates a computer system.

FIG. 14 is a block diagram illustrating an embodiment of a computer system 1600 that can be used to implement various embodiments described herein. For example, the computer system 1600 may be configured to implement the method of FIG. 2 in accordance with some embodiments. Computer system 1600 includes a bus 1602 or other communication mechanism for communicating information, and a processor 1604 coupled with the bus 1602 for processing information. The processor 1604 may be an example of the processor 54 of FIG. 1, or an example of any processor described herein. The computer system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The computer system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The computer system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the computer system 1600 can be used to perform various functions described herein. According to some embodiments, such use is provided by computer system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another computer-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "computer-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the computer system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The computer system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the computer system 1600, are exemplary forms of carrier waves transporting the information. The computer system 1600 can send messages and receive data, including program code, through the network(s), the network link 1620, and the communication interface 1618.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

The invention claimed is:

1. A method for management of treatment strategy, comprising:
   determining, using a processing unit, a first probability density function related to a first uncertainty in hitting a target in a treatment of the target;
   determining, using the processing unit, a second probability density function related to a second uncertainty, wherein the first uncertainty is attributable to a first source of uncertainty, and the second uncertainty is attributable to a second source of uncertainty that is different from the first source of uncertainty;

processing at least the first probability density function and the second probability density function using the processing unit to obtain a result for management of the treatment strategy, wherein the management of the treatment strategy is for determining one or more parameters for controlling a treatment system; and outputting the result of the processing.

2. The method of claim 1, wherein the act of processing comprises combining the first and second probability density functions by convolution to determine a composite probability density function.

3. The method of claim 2, further comprising determining a margin based on the composite probability density function.

4. The method of claim 2, further comprising determining a volume that encompasses a level of certainty derived from the composite probability density function.

5. The method of claim 4, wherein the act of determining the volume comprises determining a margin expansion.

6. The method of claim 2, wherein the result comprises the composite probability density function.

7. The method of claim 1, wherein the act of processing comprises performing a calculation using a margin as an optimization variable.

8. The method of claim 1, wherein the first probability density function is based on a motion trace.

9. The method of claim 8, wherein the motion trace is created using one or more external markers.

10. The method of claim 8, wherein the motion trace is created using one or more internal markers.

11. The method of claim 8, wherein the motion trace represents a breathing motion, a cardiac motion, or an irregular motion.

12. The method of claim 8, wherein the motion trace represents a motion of a patient for which the first probability density function is determined.

13. The method of claim 8, wherein the first probability density function is determined for a first patient, and the motion trace represents a motion of a second patient or a modeled motion.

14. The method of claim 1, wherein the first uncertainty is attributable to an accuracy of a device that measures positions.

15. The method of claim 1, wherein the first uncertainty is attributable to an accuracy of a correlation between a marker position and a tissue position.

16. The method of claim 1, wherein the first uncertainty is attributable to an accuracy in a prediction of a future position.

17. The method of claim 1, wherein the first uncertainty is attributable to an energy delivery accuracy of a treatment machine.

18. The method of claim 1, wherein the first uncertainty relates to a gating window.

19. The method of claim 1, wherein the result is output during a treatment planning session.

20. The method of claim 1, wherein the result is output during a treatment session.

21. The method of claim 1, wherein the result comprises a ranking of different motion management strategies.

22. The method of claim 21, wherein the different motion management strategies are ranked based on different respective margins, or based on different volumes derived from the different respective margins.

23. The method of claim 1, wherein the result comprises a margin.

24. The method of claim 1, wherein the result comprises information regarding a beam aperture margin.

25. The method of claim 24, further comprising:
obtaining motion data during a treatment session; and
adjusting a beam aperture based on the information regarding the beam aperture margin.

26. The method of claim 1, wherein the result comprises a volume to be treated.

27. The method of claim 1, wherein the result comprises a volume of healthy tissue.

28. The method of claim 1, further comprising adjusting a dose rate based on the result during a treatment session.

29. An apparatus for management of treatment strategy, comprising:
a processing unit configured for:
determining a first probability density function related to a first uncertainty in hitting a target in a treatment of the target;
determining a second probability density function related to a second uncertainty, wherein the first uncertainty is attributable to a first source of uncertainty, and the second uncertainty is attributable to a second source of uncertainty that is different from the first source of uncertainty;
processing at least the first probability density function and the second probability density function to obtain a result for management of the treatment strategy, wherein the management of the treatment strategy is for determining one or more parameters for controlling a treatment system; and
outputting the result of the processing.

30. The apparatus of claim 29, wherein the processing unit is configured to perform the act of processing by combining the first and second probability density functions by convolution to determine a composite probability density function.

31. The apparatus of claim 30, wherein the processing unit is further configured for determining a margin based on the composite probability density function.

32. The apparatus of claim 30, wherein the processing unit is further configured for determining a volume that encompasses a level of certainty derived from the composite probability density function.

33. The apparatus of claim 32, wherein the processing unit is configured for determining a margin expansion for determining the volume.

34. The apparatus of claim 30, wherein the result comprises the composite probability density function.

35. The apparatus of claim 29, wherein the processing unit is configured to perform the act of processing comprises performing a calculation using a margin as an optimization variable.

36. The apparatus of claim 29, wherein the processing unit is configured to receive a motion trace, and the processing unit is configured to determine the first probability density function based on a motion trace.

37. The apparatus of claim 36, wherein the motion trace is created using one or more external markers.

38. The apparatus of claim 36, wherein the motion trace is created using one or more internal markers.

39. The apparatus of claim 36, wherein the motion trace represents a breathing motion, a cardiac motion, or an irregular motion.

40. The apparatus of claim 36, wherein the motion trace represents a motion of a patient for which the first probability density function is determined.

41. The apparatus of claim 36, wherein the first probability density function is for a first patient, and the motion trace represents a motion of a second patient or a modeled motion.

42. The apparatus of claim 29, wherein the first uncertainty is attributable to an accuracy of a device that measures positions.

43. The apparatus of claim 29, wherein the first uncertainty is attributable to an accuracy of a correlation between a marker position and a tissue position.

44. The apparatus of claim 29, wherein the first uncertainty is attributable to an accuracy in a prediction of a future position.

45. The apparatus of claim 29, wherein the first uncertainty is attributable to an energy delivery accuracy of a treatment machine.

46. The apparatus of claim 29, wherein the first uncertainty relates to a gating window.

47. The apparatus of claim 29, wherein the processing unit is configured to output the result during a treatment planning session.

48. The apparatus of claim 29, wherein the processing unit is configured to output the result during a treatment session.

49. The apparatus of claim 29, wherein the result comprises a ranking of different motion management strategies.

50. The apparatus of claim 49, wherein the processing unit is configured to rank the different motion management strategies based on different respective margins.

51. The apparatus of claim 29, wherein the result comprises a margin.

52. The apparatus of claim 29, wherein the result comprises information regarding a beam aperture margin.

53. The apparatus of claim 52, wherein the processing unit is further configured for:

obtaining motion data during a treatment session; and adjusting a beam aperture based on the information regarding the beam aperture margin.

54. The apparatus of claim 29, wherein the result comprises a volume to be treated.

55. The apparatus of claim 29, wherein the result comprises a volume of healthy tissue.

56. The apparatus of claim 29, wherein the processing unit is further configured to adjust a dose rate based on the result during a treatment session.

57. A computer product having a non-transitory medium storing a set of instructions, an execution of which causes an image processing method for management of treatment strategy to be performed, the method comprising:

determining a first probability density function related to a first uncertainty in hitting a target in a treatment of the target;

determining a second probability density function related to a second uncertainty, wherein the first uncertainty is attributable to a first source of uncertainty, and the second uncertainty is attributable to a second source of uncertainty that is different from the first source of uncertainty;

processing at least the first probability density function and the second probability density function to obtain a result for management of the treatment strategy, wherein the management of the treatment strategy is for determining one or more parameters for controlling a treatment system; and outputting the result of the processing.

* * * * *